United States Patent [19]

Whitcomb

[11] Patent Number: 5,859,037
[45] Date of Patent: Jan. 12, 1999

[54] SULFONYLUREA-GLITAZONE COMBINATIONS FOR DIABETES

[75] Inventor: Randall Wayne Whitcomb, Ann Arbor, Mich.

[73] Assignee: Warner-Lambert Company, Morris Plains, N.J.

[21] Appl. No.: 970,057

[22] Filed: Nov. 13, 1997

Related U.S. Application Data

[60] Provisional application No. 60/038,224 Feb. 19, 1997.

[51] Int. Cl.$^6$ ........................ A61K 31/425; A61K 31/175
[52] U.S. Cl. ........................... 514/369; 514/593; 514/866
[58] Field of Search .................................... 514/369, 593, 514/866

[56] References Cited

FOREIGN PATENT DOCUMENTS 0 749 751 A2  12/1996  European Pat. Off. .
0 753 298 A1  1/1997  European Pat. Off. .

OTHER PUBLICATIONS

Today's News, "Rezulin(R) (troglitazone) . . . ", 1997, pp. 1–3.
Oakes et al., "A New Antidiabetic Agent . . . ", Diabetes vol. 43, 1994 p. 1203.
Hulin et al., "The Glitazone Family . . . ", Current Pharm. Design. 1996, vol. 2, No. 1, pp. 85–.
Groop et al., "Sulfonylureas in NIDDM", Diabetes Care, 1992, vol. 15, No. 6, pp. 737–754.
Nakano et al., CS–045, "Clinical Evaluation . . . ", English Transl. No. 138–007, pp. 1–38 (1993).

*Primary Examiner*—Kimberly Jordan
*Attorney, Agent, or Firm*—Charles W. Ashbrook

[57] ABSTRACT

Combinations of a sulfonylurea antidiabetic agent and a glitazone antidiabetic agent are useful for treating diabetes mellitus and improving glycemic control.

8 Claims, 6 Drawing Sheets

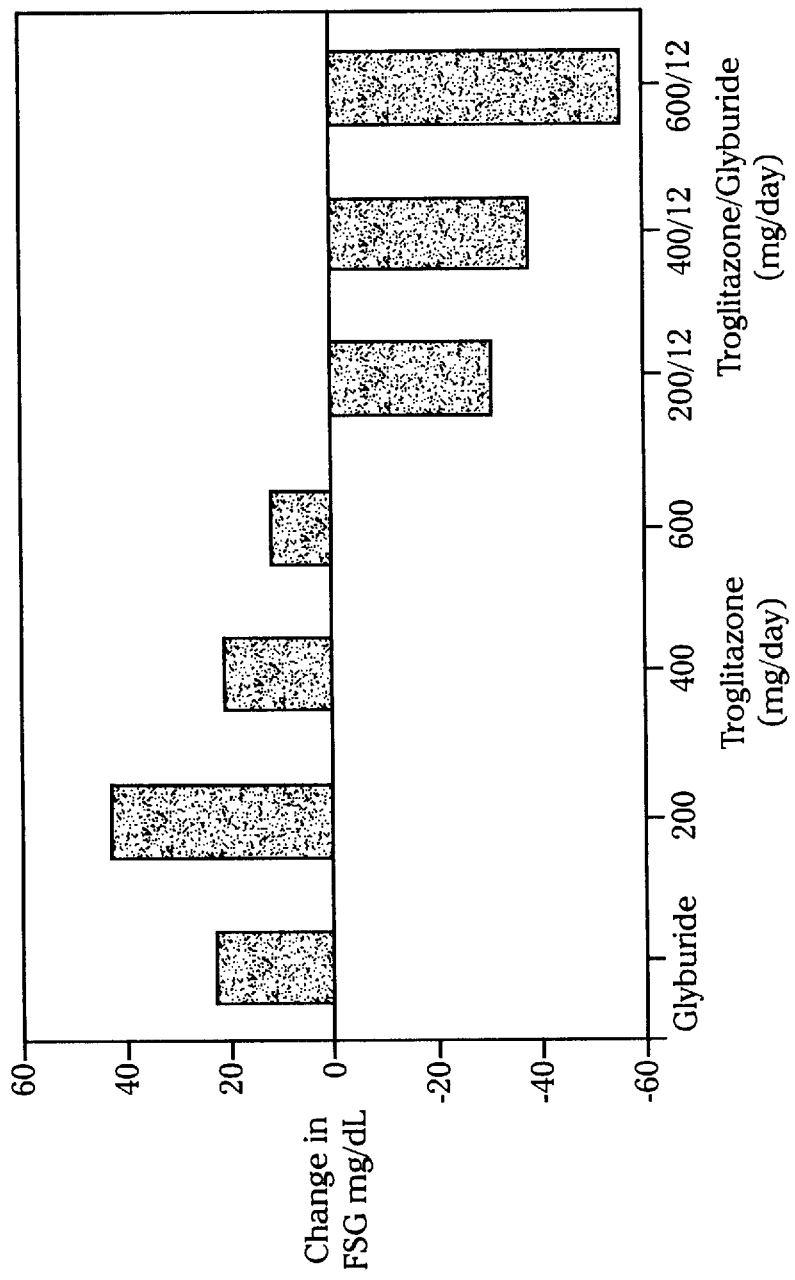

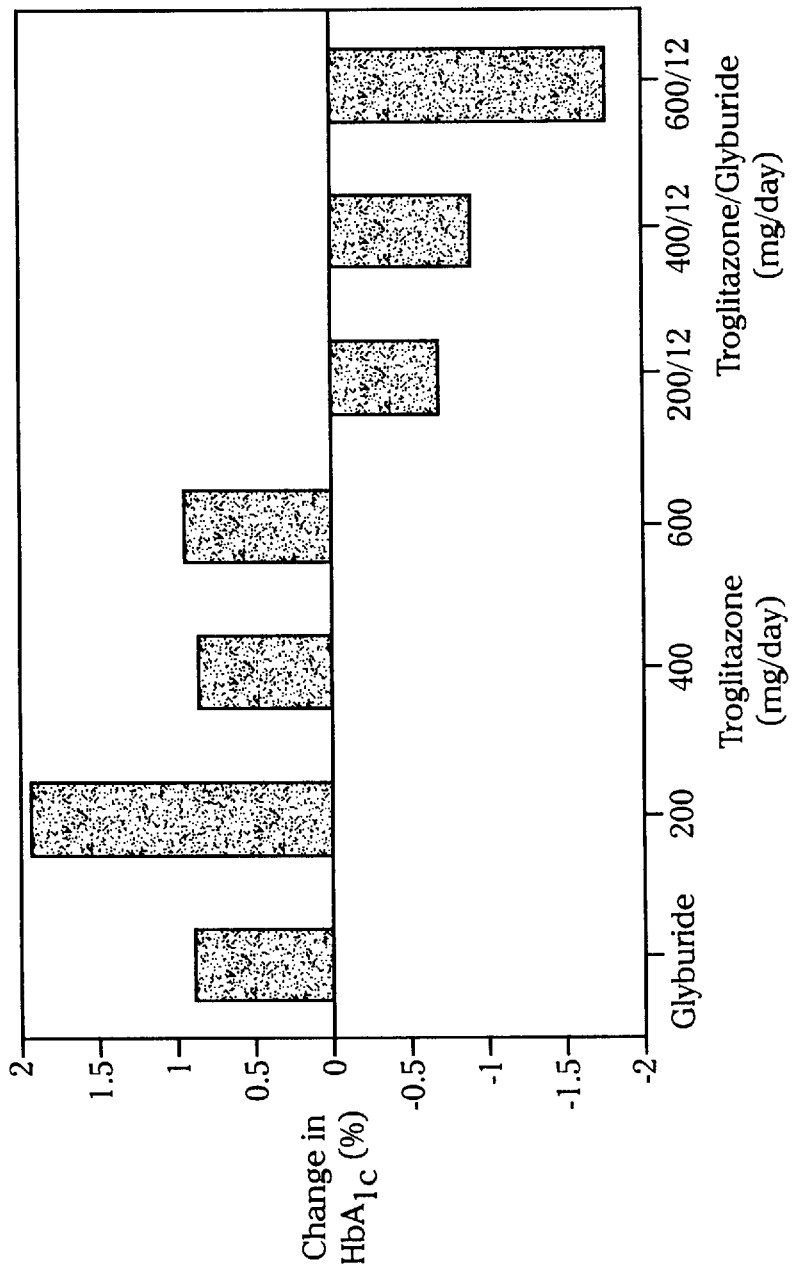
FIG-3  Mean Change From Baseline in HbA$_{1c}$ at Week 52 (ITT)

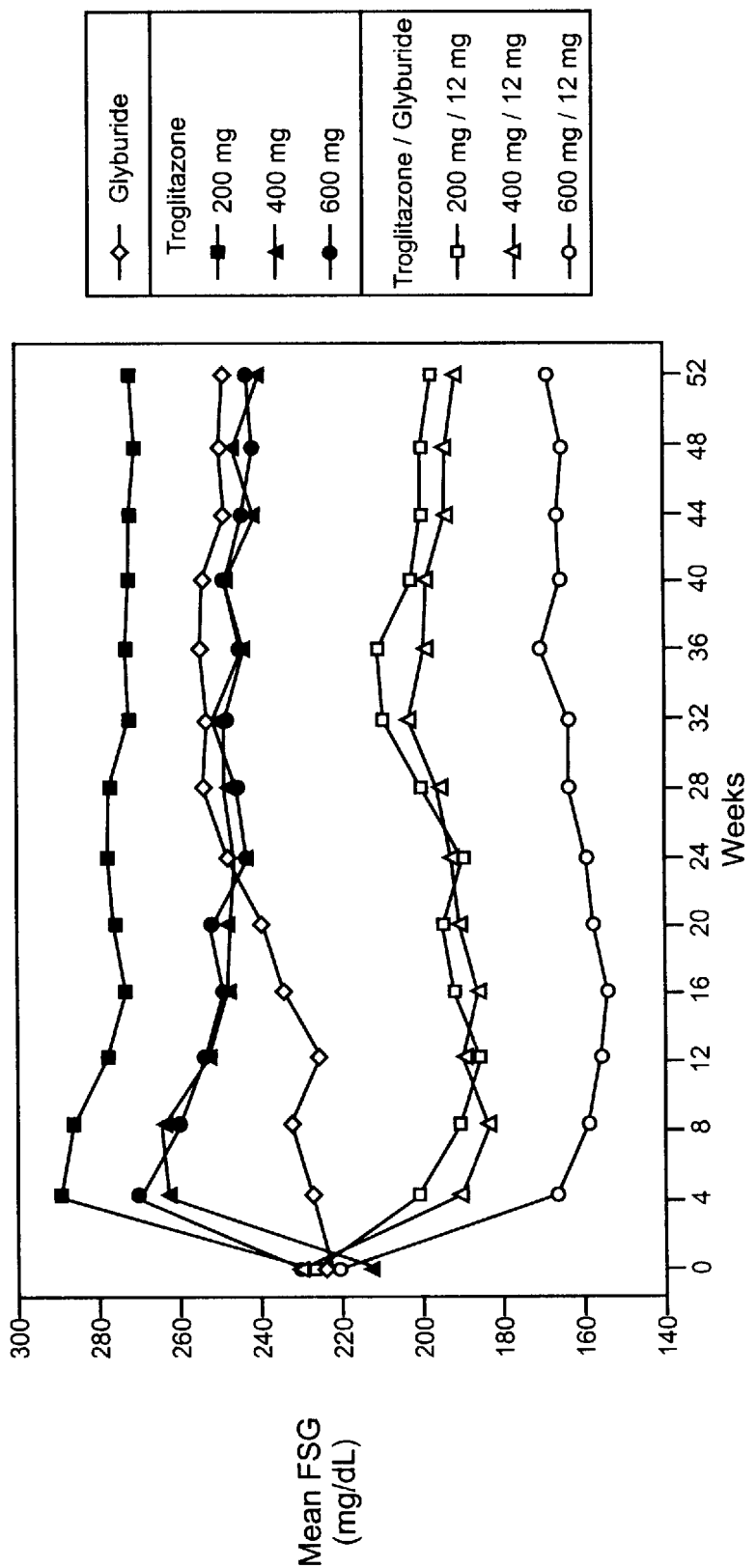
FIG-4a Mean Levels of a) FSG and b) HbA$_{1C}$ by Time (ITT) (Page 1 of 2)

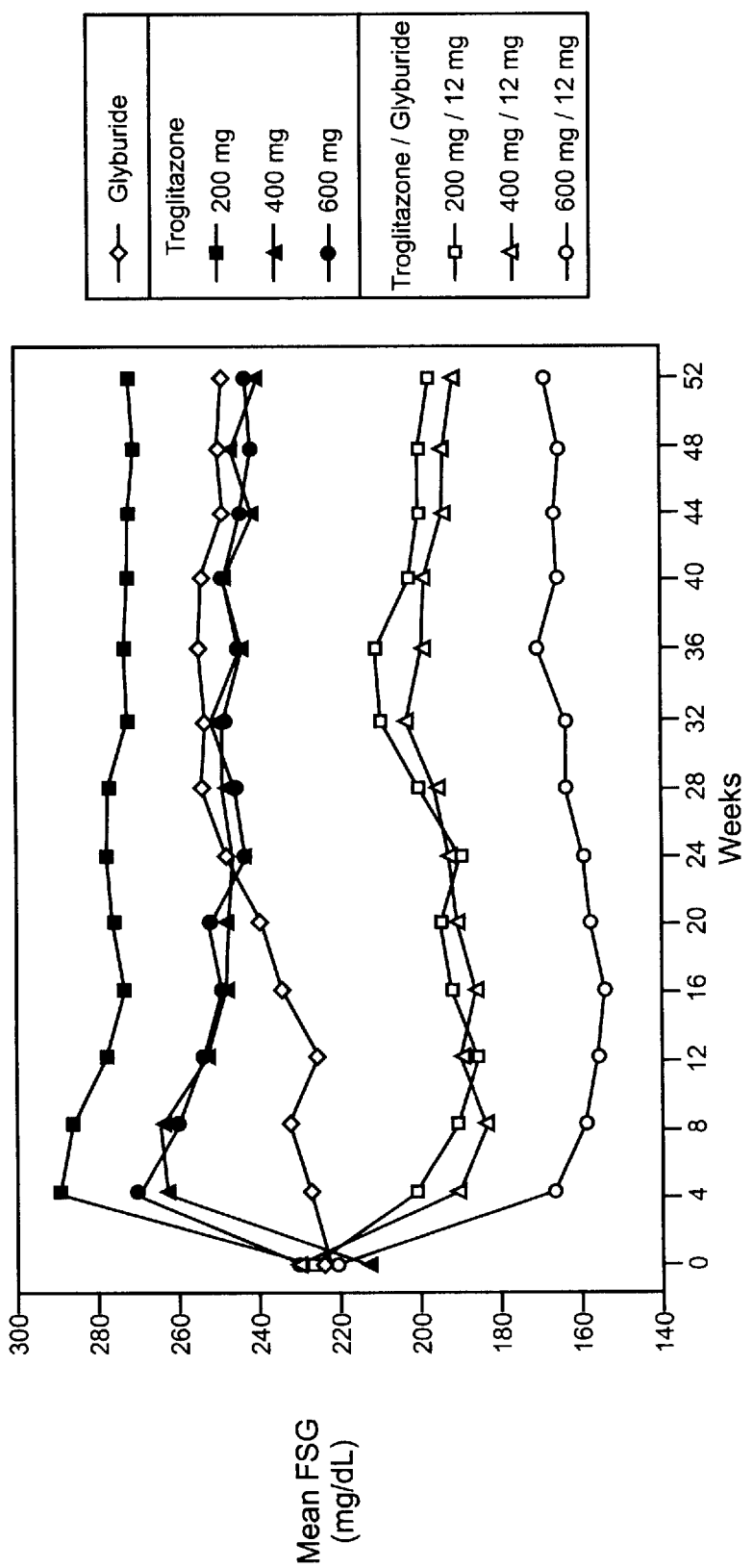
FIG-4b Mean Levels of a) FSG and b) HbA$_{1c}$ by Time (ITT) (Page 2 of 2)

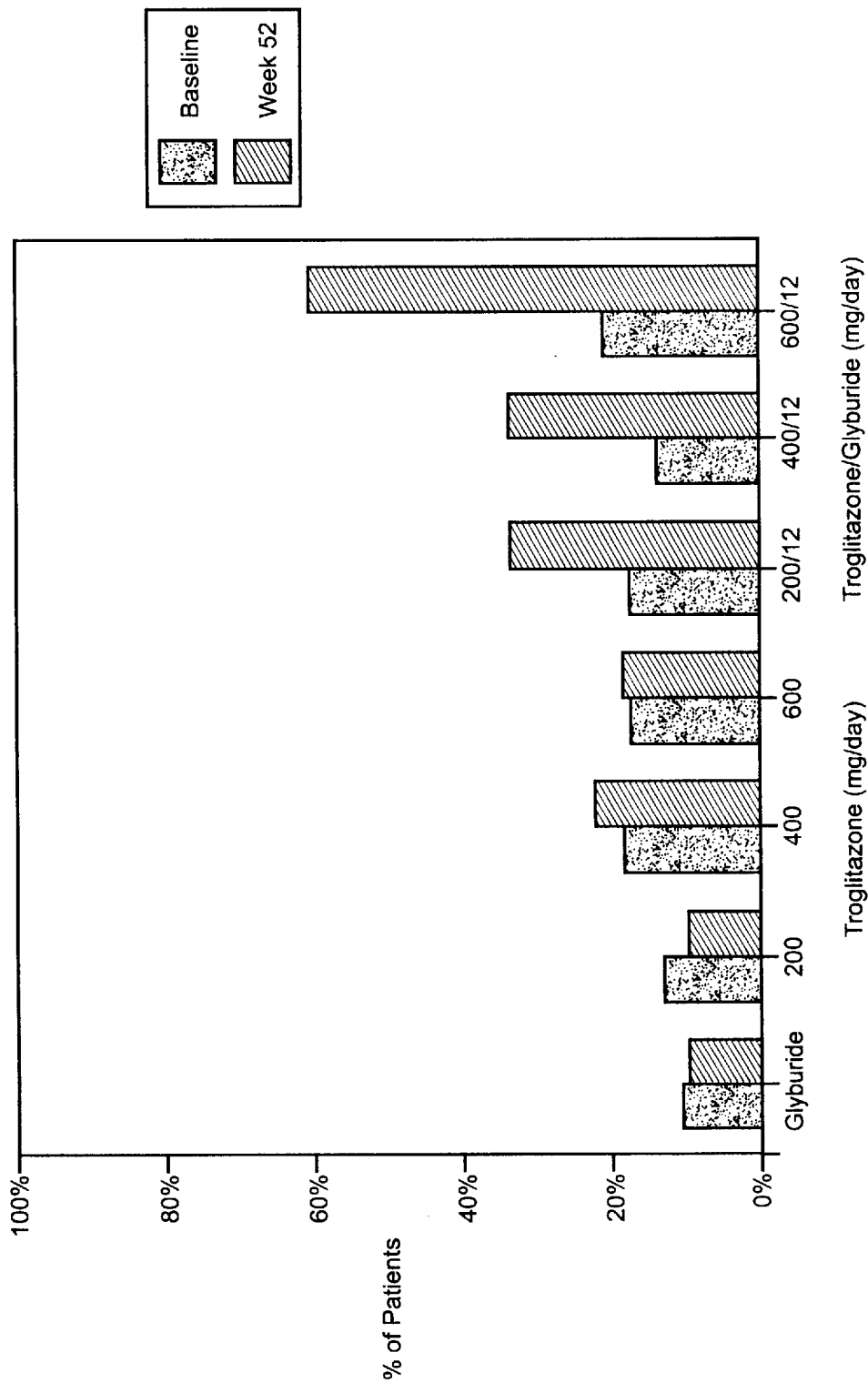

SULFONYLUREA-GLITAZONE COMBINATIONS FOR DIABETES

This application claims the benefit of U.S. Provisional Application No. 60/038,224 filed Feb. 19, 1997.

FIELD OF THE INVENTION

This invention relates to combinations of antidiabetic sulfonylurea compounds with glitazone compounds, and to a method for treating diabetes employing such combinations.

BACKGROUND OF THE INVENTION

Diabetes mellitus is a metabolic disorder characterized by hyperglycemia, insulin resistance, and is often associated with other disorders such as obesity, hypertension, hyperlipidemia, as well as complications such as cardiovascular disease, retinopathy, neuropathy, and nephropathy. The disease is progressive in nature, and can often be controlled initially by diet alone, but generally requires treatment with drugs such as sulfonylureas and injections of exogenous insulin. A new class of compounds known as the glitazones has recently received a great deal of attention for their ability to treat diabetes. These compounds operate by increasing the sensitivity of insulin receptors throughout the body, thereby diminishing or eliminating the need for exogenous insulin.

It has now been discovered that combination therapy with a sulfonylurea and a glitazone results in dramatic improvement in glycemic control. Accordingly, such combinations are especially useful in treating diabetes and associated complications.

SUMMARY OF THE INVENTION

This invention provides a method of treating diabetes by administering to a subject in need of treatment a combination of a sulfonylurea antidiabetic agent and an antidiabetic glitazone.

The sulfonylureas are a class of compounds that have been widely employed to treat diabetes. Such compounds are well known, for example as described in U.S. Pat. Nos. 3,454,635, 3,669,966, 2,968,158, 3,501,495, 3,708,486, 3,668,215, 3,654,357, and 3,097,242. Most of the sulfonylurea antidiabetics are defined by the formula

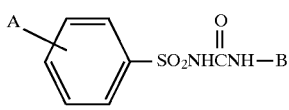

where A is hydrogen, halo, or an organic radical such as alkyl, alkanoyl, aryl, aralkyl, heteroaryl, and cycloalkyl, and B is alkyl, cycloalkyl, and a heterocyclic group such as hexahydroazepine. Preferred sulfonylureas to be employed are those wherein A is chloro, alkyl such as methyl, or alkyl substituted with aryl carbonyl or aryl carboxamido, for instance 3-chloro-5-methoxybenzoylethyl or 5-methyl-2-pyrazinylcarbonylaminoethyl.

Especially preferred sulfonylureas to be employed in the combinations of this invention are glyburide, gliquidone, glipizide, tolbutamide, tolazamide, glisoxepid, chlorpropamide, glibornuride, gliclazide, glimepiride, phenbutamide, and tolcyclamide.

According to this invention, the foregoing sulfonylureas are used in combination with a glitazone to treat diabetes and to improve glycemic control. The glitazones are a family of antidiabetic agents characterized as being thiazolidinediones or related analogs. They are described in *Current Pharmaceutical Design*, 1996;2:85–101. Typical glitazones have the formula

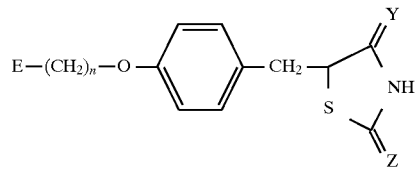

where n is 1, 2, or 3, Y and Z independently are O or NH; and E is a cyclic or bicyclic aromatic or non-aromatic ring, optionally containing a heteroatom selected from oxygen or nitrogen.

Preferred glitazones have the formula

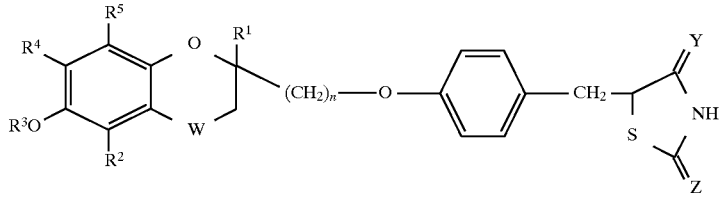

wherein:

$R^1$ and $R^2$ independently are hydrogen or $C_1$–$C_5$ alkyl;

$R^3$ is hydrogen, a $C_1$–$C_6$ aliphatic acyl group, an alicyclic acyl group, an aromatic acyl group, a heterocyclic acyl group, an araliphatic acyl group, a ($C_1$–$C_6$ alkoxy) carbonyl group, or an aralkyloxycarbonyl group;

$R^4$ and $R^5$ independently are hydrogen, $C_1$–$C_5$ alkyl, $C_1$–$C_5$ alkoxy, or $R^4$ and $R^5$ together are $C_1$–$C_4$ alkylenedioxy;

W is —$CH_2$—, >CO, or $CHOR^6$, where $R^6$ is any one of the atoms or groups defined for $R^3$ and may be the same as or different from $R^3$;

n, Y, and Z are as defined above, and pharmaceutically acceptable salts thereof.

An especially preferred glitazone is troglitazone having the formula

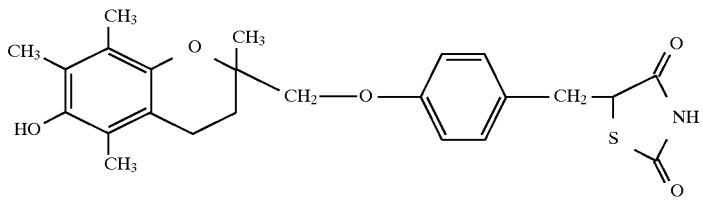

Other glitazones that can be employed in this invention are described in U.S. Pat. Nos. 5,457,109 and 5,478,852, which are incorporated herein by reference. Other specific glitazones which are preferred include ciglitazone, pioglitazone, englitazone, TA 174, which has the formula

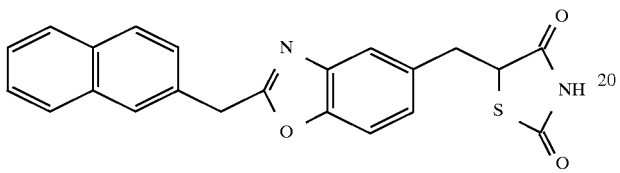

and BRL 49653 (rosiglitazone), which has the formula

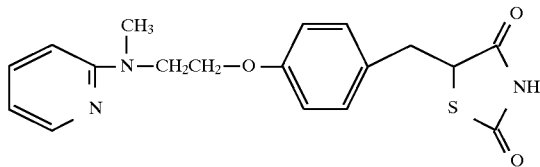

Additionally preferred glitazones include:

5-(4-[2-[1-(4-2'-Pyridylphenyl)ethylideneaminooxy] ethoxy]benzyl]thiazolidine-2,4-dione;

5-(4-[5-Methoxy-3-methylimidazo[5,4-b]pyridin-2-yl-methoxy)benzyl]thiazolidine-2,4-dione, or its hydrochloride;

5-[4-(6-Methoxy-1-methylbenzimidazol-2-yl-methoxy) benzyl]thiazolidine-2,4-dione;

5-[4-(1-Methylbenzimidazol-2-ylmethoxy)-benzyl] thiazolidine-2,4-dione; and

5-[4-(5-Hydroxy-1,4,6,7-tetramethylbenzimidazol-2-ylmethoxy)benzyl]thiazolidine-2,4-dione.

BRIEF DESCRIPTION OF THE FIGURES

FIG. 2 shows the change in fasting serum glucose (FSG) in mg/dL at Week 52 for each treatment group, and shows the dramatic reduction in FSG achieved with combination therapy according to this invention when evaluated by the insulin tolerance test (ITT).

FIG. 3 shows the percentage change in hemoglobin $A_{1c}$ ($HbA_{1c}$) in each treatment group at Week 52, and shows the dramatic reduction in $HbA_{1c}$ effected by combination therapy.

FIG. 4 shows the mean levels of FSG and $HbA_1c$ for each treatment group at various time intervals over the 52-week treatment period, and demonstrates that the majority of improvement in glycemic control (FSG) was achieved by the fourth week of combination therapy.

FIG. 5 shows the percentage distribution of patients in each treatment group with $HbA_1c$ levels less than or equal to 8% at baseline and at 52 weeks of treatment, and establishes the synergistic increase in control achieved with combination therapy.

DETAILED DESCRIPTION OF THE INVENTION

Figure 1:
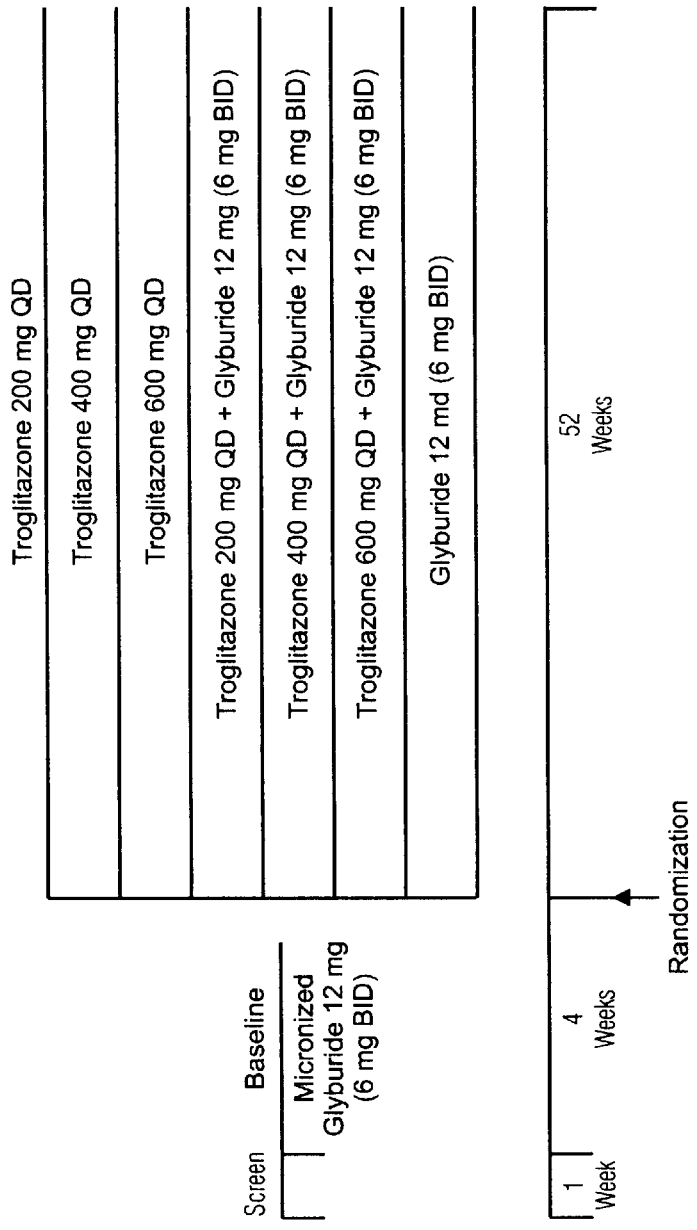
FIG. 1 shows the design of the clinical study used to establish the method of this invention and the typical medications administered to the individual study groups.

According to this invention, a sulfonylurea is used in combination with a glitazone to treat diabetes and to improve glycemic control in patients in need of treatment. The compounds can be employed individually or can be combined in a single formulation, for example as a tablet, capsule, syrup, solution, as well as controlled release formulations. In a preferred embodiment, the sulfonylurea and glitazone are formulated individually and administered in the same manner that each is normally used clinically.

The dosage of each agent will vary depending upon the severity of the disease, the frequency of administration, the particular agents and combinations utilized, and other factors routinely considered by an attending medical practitioner. The sulfonylurea normally will be administered at a daily dose of from about 0.25 mg to about 500 mg, typically about 3 mg to about 250 mg. A typical dosage for glyburide, for example, will be about 10 to about 20 mg per day. The glitazones will normally be administered at doses from about 5 mg to about 2500 mg per day, and more typically from about 50 mg to about 1500 mg per day. A preferred glitazone is troglitazone, and it will be employed at doses from about 100 mg to about 1000 mg per day.

The invention provides compositions of a sulfonylurea and a glitazone, and a method of treating diabetes and controlling glycemic conditions comprising administering to a patient in need of treatment an effective amount of a sulfonylurea and an effective amount of a glitazone. When the sulfonylurea and glitazone are formulated together, the compositions will contain about one to about 1000 parts by weight of sulfonylurea, and about 1000 to about one part by weight glitazone. For example, a typical composition of glyburide and troglitazone will contain about 12 mg of glyburide and about 500 mg of troglitazone. Such combination will be administered to an adult patient about once each day to achieve a synergistic glycemic control.

The compositions may contain common excipients and carriers such as starch, sucrose, talc, gelatin, methylcellulose, and magnesium stearate. The compositions will normally be made for oral administration, for instance as tablets or capsules, but also may be in the form of aqueous suspensions or solutions, suppositories, slow release forms, for example employing an osmotic pump, skin patch, or the like.

The method of treating diabetes employing a combination of a sulfonylurea and a glitazone has been established in a long-term controlled clinical evaluation. The study determined the efficacy and safety of troglitazone alone and in combination with the sulfonylurea glyburide for the treatment of non-insulin dependent diabetes mellitus (NIDDM). This study targeted the segment of the NIDDM population in which the disease state has progressed to a point where maximum doses of sulfonylureas no longer produce adequate glycemic control. These patients are at a stage where the maximally stimulated pancreatic insulin secretion does not keep up with the increasing demand. Since the unstimulated (absence of sulfonylurea) insulin secretory capacity of the beta cells is very low in this population, reversing insulin resistance alone would be of partial benefit. Therefore, maintaining a level of stimulated insulin secretion with a sulfonylurea while adding troglitazone to improve insulin sensitivity could provide a level of glycemic control unattainable by either medication alone.

A primary objective of the study was to assess the efficacy of troglitazone alone or in combination with micronized glyburide in patients with NIDDM by comparing changes in markers of glycemic and lipid homeostasis over 1 year of treatment. Long-term safety was also an objective of this study, assessed by adverse events and clinical laboratory data.

The effect of treatment on the pattern of postprandial glucose tolerance (standard 2-hour meal tolerance test) was determined in a subset of patients. In addition, heart mass and function (echocardiographic procedure) were monitored in a subset of patients.

Thirty centers in the US (Table 1), each with matching protocol and case report forms, participated in this study. This study was conducted according to Good Clinical Practices Guidelines. Institutional Review Board approval and informed patient consent were obtained prior to the study.

TABLE 1

List of Investigators

| Center 991-55- | State | Number of patients | |
|---|---|---|---|
| | | Randomized | Completed |
| 01 | Louisiana | 20 | 7 |
| 02 | Indiana | 27 | 16 |
| 03 | Illinois | 14 | 9 |
| 04[a] | New York | 30 | 18 |
| 05 | Georgia | 21 | 9 |
| 06[b] | Texas | 22 | 11 |
| 07[b] | Louisiana | 8 | 8 |
| 08 | Massachusetts | 12 | 5 |
| 09[b] | Missouri | 11 | 5 |
| 10 | North Carolina | 19 | 4 |
| 11 | Wisconsin | 23 | 13 |
| 12 | Florida | 29 | 20 |
| 13 | Colorado | 19 | 15 |
| 14[b] | California | 11 | 9 |
| 15 | Ohio | 14 | 11 |
| 16[b] | Michigan | 6 | 3 |
| 18[b] | Nebraska | 27 | 18 |
| 20 | California | 18 | 7 |
| 21 | Texas | 26 | 16 |
| 22 | Massachusetts | 13 | 2 |
| 23 | California | 10 | 7 |
| 24 | Colorado | 15 | 11 |
| 25 | Colorado | 32 | 13 |
| 26 | Nebraska | 35 | 22 |
| 27 | Wyoming | 11 | 8 |
| 28 | California | 23 | 16 |
| 29[b] | Michigan | 15 | 9 |
| 30 | Alabama | 9 | 5 |

TABLE 1-continued

List of Investigators

| Center 991-55- | State | Number of patients | |
|---|---|---|---|
| | | Randomized | Completed |
| 31 | Missouri | 25 | 15 |
| 32 | Michigan | 7 | 6 |
| Total | | 552 | 318 |

[a]Meal tolerance testing performed at this site.
[b]Meal tolerance and echocardiograms performed at this site.

Corning Nichols Institute was contracted to provide all testing of blood and urine samples for efficacy and safety results. Corning Hazelton (Madison, Wis.) supplied all troglitazone plasma assay results.

This was a 12-month, double-blind, randomized, parallel-group, active-control, multicenter study design (FIG. 1).

After an initial screening visit, patients meeting the inclusion criteria entered a 4-week baseline phase (unblinded) in which they received 12 mg micronized glyburide (6 mg BID). At the end of the baseline phase, patients who still exhibited a fasting serum glucose (FSG) of >140 mg/dL and <300 mg/dL were randomized to 1 of 7 blinded parallel treatment arms. Treatment consisted of troglitazone monotherapy, troglitazone/glyburide combination therapy, or glyburide monotherapy (active control).

Troglitazone was supplied in the form of 200-mg tablets (Table 2). Matching glyburide tablets were also supplied to maintain blinding.

TABLE 2

Lot/Formulation Numbers for Study Medications

| Study Medication | Lot | Formulation |
|---|---|---|
| Troglitazone 200-mg Tablet | CM 0120295 | 137070-13 |
| | CM 1581194 | 137070-13 |
| Glynase (Glyburide) | | |
| 3-mg Prestab Tablet | 202JP | marketed[a] |
| | 944JD | marketed[a] |
| 3-mg Tablet in Capsule | CM 0010195 | 137070-11 |
| | CM 0560595 | 137070-11 |
| | CM 0900694 | 137070-11 |
| | CM 1491194 | 137070-11 |
| Placebo | | |
| Tablet (Troglitazone Match) | CM 0200295 | 137070-8P |
| | CM 0780594 | 137070-8P |
| Capsule (Glynase Match) | CM 1030694 | 14964-2PAM2 |
| | CM 1481194 | 14964-2PAM2 |

[a]Used in production of 3-mg capsule

Patient Selection

Inclusion Criteria

Men or women greater than 18 years of age with NIDDM (National Diabetes Data Group criteria), a fasting C-peptide level of ≧1.5 ng/mL, FSG >140 mg/dL, and hemoglobin $A_{1c}$ ($HbA_{1c}$) levels greater than the normal range (>5.9%) were selected for the study. Patients were also required to have been receiving maximum doses of a sulfonylurea to qualify as a sulfonylurea failure.

Exclusion Criteria

Patients were excluded from the study if they had used insulin (chronically) or had a history of ketoacidosis, symptomatic diabetic neuropathy or retinopathy, or renal disease. Patients were also excluded from the study if they were of childbearing potential, had angina pectoris, congestive heart failure (Class III or IV), significant hypertension, a major vascular medical event within 3 months of the study, significant hepatic enzyme elevation, anemia, active cancer within 5 years of the study, or received another investigational drug within 1 month of screening.

Prohibited Medications

No medications were specifically prohibited for concurrent use except beta blockers, which block the acute adrenergic symptoms (the early warnings) of hypoglycemia. Previous oral antidiabetic medications were discontinued upon completion of screening and start of the baseline phase.

Dosage levels of all concurrent medications were, if medically appropriate, to remain unchanged while the patient was enrolled in the study. Of particular interest were thiazide diuretics, steroids, oral contraceptives, and calcium channel blockers, which are known to counteract the actions of sulfonylureas.

The use of insulin was prohibited except for emergency care for a period that was not to exceed 3 consecutive days.

Guidelines for Patient Withdrawal

Patients could withdraw voluntarily at any time during the study or be withdrawn by the investigator because of significant adverse events or deterioration in health, poor compliance, pregnancy, or prolonged symptomatic hyperglycemia or persistent worsening or failure to improve glycemic control as monitored by FSG. Patients who required emergency insulin use longer than 3 consecutive days were to be removed from the study.

Evaluations

Efficacy

The primary efficacy parameters included endpoints related to glucose homeostasis: FSG and $HbA_{1c}$. The change from baseline in these parameters at Week 52 compared to active control (glyburide) was the primary measure of efficacy. For patients terminating early from the study, their last observation was carried forward (LOCF) to Week 52. A decrease in these parameters was indicative of an improvement in glycemic control.

Secondary efficacy parameters included markers of glycemic homeostasis (insulin and C-peptide) and markers of lipid metabolism (total cholesterol, total triglycerides, HDL, VLDL, LDL (measured), free fatty acids, Lp(a), Apo A1, and Apo B).

The following sets of treatment comparisons were considered primary:

Comparison of each troglitazone/glyburide combination group with the glyburide-monotherapy group.

Comparison of each troglitazone-monotherapy group with the glyburide-monotherapy group.

The following sets of treatment comparisons were considered secondary:

Comparison of each troglitazone monotherapy group with the corresponding troglitazone/glyburide combination group.

Pairwise comparisons of troglitazone monotherapy groups.

Pairwise comparisons of troglitazone/glyburide combination groups.

A 2-hour meal tolerance test to assess postprandial glucose and insulin excursions in response to a premeasured meal (breakfast) was conducted in a subset of patients at baseline, Week 24, and at the end of treatment. The change from baseline in the area under the glucose concentration-time curve [AUC(0–2 hr)] compared with that for glyburide was assessed. Additional parameters included total insulin and C-peptide. Analyses of the meal tolerance parameters were based on observations at the end of treatment; observations from Week 24 were not carried forward.

Pharmacokinetics

Trough plasma concentrations of troglitazone were determined at Week 12. Blood samples (7 mL) were collected in heparinized glass tubes. Following centrifugation, plasma samples were transferred to plastic tubes and stored at −20° C. until assayed.

Plasma samples were assayed at Corning Hazleton, Inc., PO Box 7545, Madison, Wis., 53707, using a validated liquid chromatographic method with electrochemical detection. The minimum quantitation limit for troglitazone was 5 ng/mL. Concentrations below the limit of quantitation were reported as zero. The analysts remained blinded to the treatment randomization code during sample analysis.

Mean and percent relative standard deviation (%RSD) values of trough troglitazone concentrations were calculated for each treatment group using SAS 6.08.

Quality of Life (QOL) Assessments

QOL was assessed by a self-administered questionnaire designed to assess health status, as perceived by the patient, just prior to treatment and at Weeks 12, 24, and 52. The questionnaire consisted of the SF-36 Health Survey and a Diabetes-Related Symptoms section.

Safety

A complete physical examination and ECG were performed during screening and at the end of the study. Clinical laboratory parameters and vital signs including blood pressure were monitored throughout the study for safety reasons. Adverse events were recorded during clinic visits and evaluated by the investigator for intensity and relationship to study drug. Reduction in the daily dose of micronized glyburide could occur in cases of documented hypoglycemia.

The effect of troglitazone treatment on heart mass and function was assessed in a subset of patients by measuring left ventricular mass index (LVMI), cardiac index (CI), stroke volume index (SVI), and peripheral resistance (R) at baseline and following 6 and 12 months of treatment. Analyses of cardiac function are based on data at the study end point; observations from Month 6 were not carried forward.

All patients randomized to treatment were included in all safety evaluations.

Clinical Observations and Laboratory Measurements

The schedule of study visits and procedures is presented in Table 3. Patients were instructed to fast overnight prior to visits requiring specimen collection.

TABLE 3

Timetable and Visit Procedures
(Page 1 of 2)

| Phase | Screening | Baseline | | |
|---|---|---|---|---|
| Length (Week) | 1 | 4 | | |
| Week | −5 | −4 | −2 | −1 |
| Medical History | X | | | |
| Physical Exam | | X | | |
| 12-Lead ECG | | X | | |
| Diet Instruction/Assessment | | X | | |
| Weight, Pulse, Blood Pressure | X | X | X | |
| Concurrent Med Query and AE Query | X | X | X | X |
| Diabetic Symptoms Assessment | X | X | | |
| Laboratory Panel (Safety Parameters)[a] | X | X | X | X |
| Laboratory Panel (Glycemic Indicators)[c] | X | X | X | X |
| Laboratory Panel (Lipid Indicators 1)[d] | | X | | X |
| Laboratory Panel (Lipid Indicators 2)[e] | | | | X |
| Discontinue Prior Antidiabetic Drug | | X | | |
| Dispense Study Drug | | X | X | |
| Verify Patient Compliance | | | X | |
| Quality of Life Questionnaire | | | | |

Timetable and Visit Procedures
(Page 2 of 2)

| Phase | Active Treatment 52 Weeks | | | | | | | | | | | | | |
|---|---|---|---|---|---|---|---|---|---|---|---|---|---|---|
| Week | 0 | 4 | 8 | 12 | 16 | 20 | 24 | 28 | 32 | 36 | 40 | 44 | 48 | 52 |
| Medical History | | | | | | | | | | | | | | |
| Physical Exam | | | | | | | | | | | | | | X |
| 12-Lead ECG | | | | | | | | | | | | | | X |
| Diet Instruction/Assessment | | | | | | | | | | | | | | |
| Weight, Pulse, Blood Pressure | X | X | X | X | X | X | X | X | X | X | X | X | X | X |
| Concurrent Med Query and AE Query | X | X | X | X | X | X | X | X | X | X | X | X | X | X |
| Diabetic Symptoms Assessment | X | X | X | X | X | X | X | X | X | X | X | X | X | X |
| Laboratory Panel (Safety Parameters)[a] | X | X | X | X[b] | X | X | X | X | X | X | X | X | X | X |
| Laboratory Panel (Glycemic Indicators)[c] | X | X | X | X | X | X | X | X | X | X | X | X | X | X |
| Laboratory Panel (Lipid Indicators 1)[d] | X | X | X | X | | X | | | | X | | | X | X |
| | | | | | X | X | | | | | | | X | X |
| Laboratory Panel (Lipid Indicators 2)[e] | X | | | | X | X | | | | | | | X | X |
| Discontinue Prior Antidiabetic Drug | | | | | | | | | | | | | | |
| Dispense Study Drug | X | X | X | X | X | X | X | X | X | X | X | X | X | |
| Verify Patient Compliance | X | X | X | X | X | X | X | X | X | X | X | X | X | X |
| Quality of Life Questionnaire | X | | | X | | | X | | | | | | | X |

[a]Safety parameters are listed in Appendix X.
[b]Sample for Drug Level Analysis also.
[c]Glycemic indicators included FSG, $HbA_{1c}$, insulin, C-peptide.
[d]Lipid Indicator 1 included total cholesterol, triglycerides, free fatty acids, LDL (measured), HDL, and VLDL (Beta Quant)
[e]Lipid Indicator 2 included Apo A1, Apo B, and Lp(a).

Data Evaluability

Efficacy analysis was performed on 2 patient populations, intent-to-treat and completers. The intent-to-treat comprised all patients randomized to treatment who had a baseline measurement and at least one follow-up measurement taken after randomization. Patients withdrawing from the study before Week 52 were included in the analysis using the LOCF procedure; the last measurement on treatment was substituted for the missing Week 52 measurement. The intent-to-treat patient sample was the primary sample for assessing efficacy. Completers comprised patients in the intent-to-treat sample who completed Week 52.

Safety analysis was performed on all patients randomized to treatment.

STATISTICAL METHODS

Efficacy Analysis

The analysis of change from baseline to Week 52 was performed using analysis of covariance (ANCOVA). The primary model included effects due to treatment and center and baseline as covariate. Treatment-by-baseline and treatment-by-center interactions were also examined in supplemental models.

For the primary comparisons of glyburide versus each combination, step-down tests for linear trend in dose response were performed based on the primary model.

For the remaining primary pairwise comparisons of glyburide versus each monotherapy, t-tests were performed using the MSE from the analysis of covariance (with a Bonferroni-Holm adjustment). For all comparisons with glyburide, 95 confidence intervals are provided using Dunnett's test.

All tests were 2-sided and conducted at $\alpha=0.05$. The level of significance for the primary treatment comparisons was adjusted for multiplicity. The adjustment was performed within each set of primary treatment comparisons. The level of significance was not adjusted for the secondary treatment comparisons.

Primary Efficacy Parameters

Summary statistics for baseline, follow-up (post-randomization), and change from baseline in $HbA_1c$ and FSG were computed by treatment group and visit. For each patient, the baseline measurement for a given parameter was defined as the measurement at Week 0.

The effect of baseline covariates such as age, gender, race, body mass index, and duration of diabetes was investigated.

Secondary Efficacy Parameters

Fasting Lipid Parameters, C-Peptide, Insulin, and Blood Pressure

Summary statistics for baseline, follow-up (post-randomization), and change from baseline in secondary efficacy parameters were computed by treatment group and visit. For each patient, the baseline measurements for insulin, C-peptide, blood pressure, total cholesterol, triglycerides, LDL, HDL, VLDL, and free fatty acids were defined as the measurement at Week 0. In order to reduce variability, the baseline Apo A, Apo B, and Lp(a) levels were defined as the average of the respective measurements at Weeks −1 and 1. Similarly, the end-of-treatment Apo A, Apo B, and Lp(a) measurements were defined as the average of the respective measurements at Weeks 48 and 52. Averages from Weeks 20 and 24 were not carried forward for these special lipid parameters.

Hemoglobin $A_{1c}$ and Glucose Responders

Patients achieving at least a 1% absolute reduction from baseline in hemoglobin $A_{1c}$ were defined as responders. The frequency distribution (number and percentage) of responders were provided by treatment group and visit. For the set of primary treatment comparisons concerning glyburide versus combination therapy, step-down comparisons of responders in each treatment group versus the glyburide group were performed by sequential application of the Cochran-Mantel-Haenszel (CMH) test for linear trend with study centers as strata. Primary comparisons of glyburide versus troglitazone monotherapy were conducted using the CMH test for general association with a Bonferroni-Holm adjustment for the 3 comparisons. The CMH test for general association were also used to perform the secondary treatment comparisons as supplemental analysis.

A similar analysis was performed on glucose responders defined as patients with at least a 30 mg/dL reduction in fasting glucose from baseline.

Meal Tolerance

Summary statistics for glucose, insulin, and C-peptide levels every 30 minutes for 2 hours were provided at baseline, and Months 6 and 12. The following response variables were analyzed: the area under the curve (AUC) of the changes from baseline from 0 to 2 hours, the change from baseline in the above parameters at 2 hours, and tmax for insulin at baseline and Month 12.

The change from baseline in each response variable was compared between treatment groups using analysis of covariance. The analysis included all patients who had baseline and Month 12 test data. The primary model included effects due to treatment and center and baseline as covariate. The 95% confidence interval for the treatment difference based on the primary model was provided for each pairwise comparison of treatment groups.

Safety Analysis

Medical history, physical examination, vital signs, biochemical parameters, electrocardiograms, and adverse events were summarized.

Summary statistics were provided for cardiac mass and function parameters (LVMI and CI). For each parameter, the 95% confidence interval for the difference between each treatment group and the glyburide group in mean change from baseline was developed. The analysis at Month 12 was performed using completer patients.

Although troglitazone monotherapy has not caused hypoglycemia in patients studied to date, combination therapy or glyburide monotherapy may potentially result in hypoglycemia. Hypoglycemia, defined as an FSG <50 mg/dL (verified laboratory value), was to be recorded as an adverse event.

PATIENT DEMOGRAPHICS, TREATMENT, AND DISPOSITION

Characteristics of Total Patient Sample

Characteristics of all patients randomized to treatment are summarized in Table 4; overall, 40% of the patients were women and 26% were $\geq 65$ years of age (mean age 58 years). Patients were evenly distributed across treatment groups with respect to sex and race. Mean age, duration of diabetes, and body mass index (BMI) were also similar across treatments. The mean BMI of 32 mg/kg$^2$ indicates that, in general, the patients were obese. Overall, the mean duration of diabetes was greater than 8 years; mean FSG was 224 mg/dL and mean $HbA_1c$ was 9.6%, indicating that these patients were generally in poor glycemic control at baseline.

Approximately one-third of the patients had a mother or a father who also had diabetes. There was also a high incidence of macrovascular complications in family members, such as heart attack, stroke, and congestive heart failure.

TABLE 4

Patient Characteristics at Baseline - All Patients
(Page 1 of 4)

| | Troglitazone Monotherapy | | |
|---|---|---|---|
| | 200 mg<br>N = 78 | 400 mg<br>N = 81 | 600 mg<br>N = 78 |
| Sex, N (%) | | | |
| Men | 40 (51.3) | 43 (53.1) | 48 (61.5) |
| Women | 38 (48.7) | 38 (46.9) | 30 (38.5) |
| Postmenopausal | 29 (37.2) | 31 (38.3) | 22 (28.2) |
| Age, yr | | | |
| Mean (SD) | 58.5 (10.4) | 58.9 (10.6) | 56.4 (10.2) |
| Median | 60.5 | 61.0 | 58.5 |
| Min, Max | 35.0, 75.0 | 32.0, 91.0 | 35.0, 76.0 |
| <65 years, N (%) | 52 (66.7) | 61 (75.3) | 61 (78.2) |
| ≧65 years, N (%) | 26 (33.3) | 20 (24.7) | 17 (21.8) |
| Race, N (%) | | | |
| White/Caucasian | 63 (80.8) | 64 (79.0) | 59 (75.6) |
| Black | 5 (6.4) | 6 (7.4) | 4 (5.1) |
| Hispanic | 10 (12.8) | 11 (13.6) | 11 (14.1) |
| Asian | 0 (0.0) | 0 (0.0) | 0 (0.0) |
| Native American | 0 (0.0) | 0 (0.0) | 2 (2.6) |
| Other | 0 (0.0) | 0 (0.0) | 2 (2.6) |
| Duration of Diabetes, yr | | | |
| Mean (SD) | 8.6 (5.7) | 8.8 (7.8) | 7.7 (5.5) |
| Median | 8.0 | 7.0 | 6.0 |
| Min, Max | <1, 27.0 | <1, 40.0 | 1.0, 30.0 |
| Body Mass Index (BMI), kg/m$^2$ | | | |
| Mean (SD) | 32.7 (6.7) | 34.0 (7.9) | 32.3 (7.1) |
| Median | 30.5 | 33.0 | 30.5 |
| Min, Max | 22.2, 53.8 | 20.6, 58.4 | 20.5, 54.5 |

Patient Characteristics at Baseline - All Patients
(Page 2 of 4)

| | Combination Therapy: Troglitazone/Glyburide | | | Glyburide | |
|---|---|---|---|---|---|
| | 200 mg/12 mg<br>N = 78 | 400 mg/12 mg<br>N = 76 | 600 mg/12 mg<br>N = 82 | Monotherapy<br>N = 79 | Grand Total<br>N = 552 |
| Sex, N (%) | | | | | |
| Men | 54 (69.2) | 50 (65.8) | 49 (59.8) | 49 (62.0) | 333 (60.3) |
| Women | 24 (30.8) | 26 (34.2) | 33 (40.2) | 30 (38.0) | 219 (39.7) |
| Postmenopausal | 19 (24.4) | 17 (22.4) | 22 (26.8) | 27 (34.2) | 167 (30.3) |
| Age, yr | | | | | |
| Mean (SD) | 56.9 (10.4) | 57.1 (10.2) | 56.3 (11.6) | 58.7 (10.8) | 57.5 (10.6) |
| Median | 56.0 | 57.5 | 56.5 | 59.0 | 58.0 |
| Min, Max | 28.0, 80.0 | 30.0, 76.0 | 32.0, 87.0 | 33.0, 87.0 | 28.0, 91.0 |
| <65 years, N (%) | 59 (75.6) | 56 (73.7) | 64 (78.0) | 56 (70.9) | 409 (74.1) |
| ≧65 years, N (%) | 19 (24.4) | 20 (26.3) | 18 (22.0) | 23 (29.1) | 143 (25.9) |
| Race, N (%) | | | | | |
| White/Caucasian | 54 (69.2) | 62 (81.6) | 61 (74.4) | 61 (77.2) | 424 (76.8) |
| Black | 11 (14.1) | 4 (5.3) | 5 (6.1) | 5 (6.3) | 40 (7.2) |
| Hispanic | 12 (15.4) | 9 (11.8) | 14 (17.1) | 12 (15.2) | 79 (14.3) |
| Asian | 1 (1.3) | 1 (1.3) | 1 (1.2) | 0 (0.0) | 3 (0.5) |
| Native American | 0 (0.0) | 0 (0.0) | 0 (0.0) | 0 (0.0) | 2 (0.4) |
| Other | 0 (0.0) | 0 (0.0) | 1 (1.2) | 1 (1.3) | 4 (0.7) |
| Duration of Diabetes, yr | | | | | |
| Mean (SD) | 8.7 (6.1) | 8.7 (5.9) | 7.7 (6.1) | 9.0 (8.4) | 8.4 (6.6) |
| Median | 7.0 | 7.0 | 5.5 | 7.0 | 7.0 |
| Min, Max | 1.0, 30.0 | <1, 31.0 | 1.0, 39.0 | 1.0, 57.0 | <1, 57.0 |
| Body Mass Index (BMI), kg/m$^2$ | | | | | |
| Mean (SD) | 31.3 (5.0) | 31.2 (5.7) | 31.5 (6.9) | 31.9 (6.1) | 32.1 (6.6) |
| Median | 30.2 | 29.8 | 30.1 | 31.1 | 30.5 |
| Min, Max | 21.3, 47.5 | 21.2, 48.4 | 21.7, 58.9 | 23.5, 54.4 | 20.5, 58.9 |

TABLE 4-continued

Patient Characteristics at Baseline - All Patients
(Page 3 of 4)

| | Troglitazone Monotherapy | | |
|---|---|---|---|
| | 200 mg<br>N = 78 | 400 mg<br>N = 81 | 600 mg<br>N = 78 |
| Waist-Hip Ratio, CM | | | |
| Means (SD) | 1.0 (0.1) | 1.0 (0.1) | 1.0 (0.1) |
| Median | 0.9 | 1.0 | 1.0 |
| Min, Max | 0.8, 1.2 | 0.8, 1.3 | 0.8, 1.2 |
| Weight, lb | | | |
| Mean (SD) | 202 (41.2) | 218 (53.1) | 207 (45.8) |
| Median | 194 | 214 | 201 |
| Min, Max | 133, 292 | 121, 380 | 127, 312 |
| FSG, mg/dL | | | |
| Mean (SD) | 226.3 (45.5) | 214.1 (50.1) | 229.8 (48.6) |
| Median | 228.5 | 221.0 | 219.0 |
| Min, Max | 124, 324 | 97, 321 | 115, 358 |
| $HbA_{1c}$, % | | | |
| Mean (SD) | 9.5 (1.4) | 9.4 (1.4) | 9.7 (1.7) |
| Median | 9.5 | 9.5 | 9.8 |
| Min, Max | 6.4, 12.9 | 6.3, 13.4 | 5.7, 13.4 |
| Total Insulin, $\mu$IU, mL | | | |
| Mean (SD) | 32.3 (30.6) | 32.7 (18.2) | 30.3 (17.5) |
| Median | 26.2 | 27.8 | 22.3 |
| Min, Max | 8.1, 264 | 8.9, 110 | 9.4, 101 |
| C-Peptide, ng/mL | | | |
| Mean (SD) | 2.9 (1.1) | 3.1 (1.2) | 3.0 (1.2) |
| Median | 2.8 | 2.9 | 2.9 |
| Min, Max | 1.1, 9.0 | 1.1, 7.1 | 1.4, 8.4 |

Patient Characteristics at Baseline - All Patients
(Page 4 of 4)

| | Combination Therapy: Troglitazone/Glyburide | | | Glyburide<br>Monotherapy<br>N = 79 | Grand Total<br>N = 552 |
|---|---|---|---|---|---|
| | 200 mg/12 mg<br>N = 78 | 400 mg/12 mg<br>N = 76 | 600 mg/12 mg<br>N = 82 | | |
| Waist-Hip Ratio, CM | | | | | |
| Means (SD) | 1.0 (0.1) | 1.0 (0.1) | 1.0 (0.1) | 1.0 (0.1) | 1.0 (0.1) |
| Median | 1.0 | 1.0 | 1.0 | 0.9 | 1.0 |
| Min, Max | 0.8, 1.1 | 0.8, 1.1 | 0.8, 1.1 | 0.8, 1.5 | 0.8, 1.5 |
| Weight, lb | | | | | |
| Mean (SD) | 204 (37.4) | 201 (43.1) | 198 (44.7) | 206 (49.1) | 205 (45.4) |
| Median | 206 | 194 | 191 | 199 | 199 |
| Min, Max | 105, 312 | 102, 324 | 115, 327 | 124, 389 | 102, 389 |
| FSG, mg/dL | | | | | |
| Mean (SD) | 225.7 (51.0) | 230.9 (42.6) | 220.2 (51.0) | 222.2 (41.2) | 224.0 (47.4) |
| Median | 223.0 | 234.0 | 217.5 | 224.0 | 225.0 |
| Min, Max | 126, 443 | 146, 329 | 120, 338 | 141, 319 | 97, 443 |
| $HbA_{1c}$, % | | | | | |
| Mean (SD) | 9.5 (1.3) | 9.7 (1.3) | 9.4 (1.5) | 9.6 (1.2) | 9.6 (1.4) |
| Median | 9.5 | 9.8 | 9.5 | 9.7 | 9.6 |
| Min, Max | 6.2, 12.4 | 6.2, 12.5 | 5.9, 13.0 | 6.6, 12.4 | 5.7, 13.4 |
| Total Insulin, $\mu$IU, mL | | | | | |
| Mean (SD) | 28.2 (13.3) | 24.8 (10.6) | 26.7 (13.9) | 27.3 (14.2) | 28.9 (18.1) |
| Median | 25.0 | 23.9 | 22.6 | 25.8 | 25.1 |
| Min, Max | 8.8, 72.0 | 5.8, 51.7 | 6.3, 80.7 | 6.8, 72.0 | 5.8, 264 |
| C-Peptide, ng/mL | | | | | |
| Mean (SD) | 2.8 (1.1) | 2.6 (0.9) | 2.9 (1.1) | 2.7 (0.9) | 2.8 (1.1) |
| Median | 2.6 | 2.5 | 2.8 | 2.6 | 2.7 |
| Min, Max | 0.9, 6.5 | 1.0, 6.8 | 1.2, 8.2 | 0.8, 4.4 | 0.8, 9.0 |

SD = Standard deviation.

Extent of Exposure

Study Medications

Table 5 summarizes patient exposure to study medication. Twenty-eight to 46% of patients completed 52 weeks of troglitazone monotherapy; 71% to 85% of patients completed 52 weeks of combination therapy. Greater than (or equal to) 92% of patients were compliant throughout the study (based on investigators assessment of compliance).

TABLE 5

Duration of Exposure to Study Medication
[Number (%) of Patients]
(Page 1 of 2)

|  | Troglitazone Monotherapy | | |
| --- | --- | --- | --- |
| Completed at Least[a] | 200 mg<br>N = 78 | 400 mg<br>N = 81 | 600 mg<br>N = 78 |
| 1 Dose | 78 (100) | 81 (100) | 78 (100) |
| 4 Weeks | 78 (100) | 81 (100) | 78 (100) |
| 8 Weeks | 69 (88.5) | 67 (82.7) | 72 (92.3) |
| 12 Weeks | 52 (66.7) | 61 (75.3) | 66 (84.6) |
| 24 Weeks | 38 (48.7) | 44 (54.3) | 48 (61.5) |
| 36 Weeks | 25 (32.1) | 39 (48.1) | 38 (48.7) |
| 52 Weeks | 22 (28.2) | 37 (45.7) | 34 (43.6) |
| Summary of Exposure, Weeks | | | |
| Mean (SD) | 26 (19) | 31 (22) | 33 (19) |
| Median (Min, Max) | 21 (1,57) | 25 (1,60) | 27 (1,59) |

Duration of Exposure to Study Medication
[Number (%) of Patients]
(Page 2 of 2)

|  | Combination Therapy:<br>Troglitazone/Glyburide | | | Glyburide |
| --- | --- | --- | --- | --- |
| Completed at Least[a] | 200 mg/<br>12 mg<br>N = 78 | 400 mg/<br>12 mg<br>N = 76 | 600 mg/<br>12 mg<br>N = 82 | Mono-<br>therapy<br>N = 79 |
| 1 Dose | 78 (100) | 76 (100) | 82 (100) | 79 (100) |
| 4 Weeks | 78 (100) | 76 (100) | 80 (97.6) | 79 (100) |
| 8 Weeks | 77 (98.7) | 74 (97.4) | 80 (97.6) | 78 (98.7) |
| 12 Weeks | 76 (97.4) | 72 (94.7) | 79 (96.3) | 77 (97.5) |
| 24 Weeks | 72 (92.3) | 63 (82.9) | 76 (92.7) | 67 (84.8) |
| 36 Weeks | 60 (76.9) | 59 (77.6) | 72 (87.8) | 56 (70.9) |

TABLE 5-continued

| 52 Weeks | 55 (70.5) | 55 (72.4) | 70 (85.4) | 45 (57.0) |
| --- | --- | --- | --- | --- |
| Summary of Exposure, Weeks | | | | |
| Mean (SD) | 45 (13) | 44 (16) | 48 (12) | 42 (15) |
| Median (Min, Max) | 52 (4,60) | 52 (1,60) | 52 (0,56) | 52 (3,60) |

[a]Study weeks defined in Appendix D.1.

Concurrent Medications and Prior Antidiabetic Medications

The majority of patients (95%–99%) were taking one or more concurrent medications. The most common concurrent medications across treatments were cardiovascular agents, musculoskeletal agents (analgesics), and anti-infectives. These types of medications were not expected to impact study results.

All patients had been receiving an antidiabetic medication prior to the study as required by the protocol. The majority had been receiving the sulfonylureas glyburide (68%–77%) or glipizide (22%–29%).

Patient Disposition

Three hundred eighteen patients (58%) completed the study as determined by the investigator (Table 6). Completion rates were highest for patients treated with combination therapy (71%–85%) and lowest for patients treated with troglitazone monotherapy (28%–44%); patients treated with glyburide monotherapy had a completion rate of 58%.

The most common reason for withdrawal was lack of efficacy, which ranged from a high of 55% for patients treated with 200 mg troglitazone to a low of 4% for patients treated with 600 mg troglitazone/12 mg glyburide combination therapy. Twenty-five percent of patients treated with glyburide monotherapy withdrew due to lack of efficacy. Withdrawal rates due to adverse events were comparable across all treatment groups.

TABLE 6

Patient Disposition
[Number (%) of Patients]
(Page 1 of 2)

|  | Troglitazone Monotherapy | | |
| --- | --- | --- | --- |
|  | 200 mg | 400 mg | 600 mg |
| Randomized to Treatment | 78 | 81 | 78 |
| Withdrawn Prior to End of Treatment | | | |
| Lack of Efficacy | 43 (55.1) | 32 (39.5) | 34 (43.6) |
| Adverse Event | 6 (7.7) | 7 (8.6) | 6 (7.7) |
| Lack of Compliance | 3 (3.8) | 2 (2.5) | 3 (3.8) |
| Pregnancy | 0 (0.0) | 1 (1.2) | 0 (0.0) |
| Other | 4 (5.1) | 3 (3.7) | 1 (1.3) |
| Total | 56 (71.8) | 45 (55.6) | 44 (56.4) |
| Completed Study[a] | 22 (28.2) | 36 (44.4) | 34 (43.6) |

TABLE 6-continued

Patient Disposition
[Number (%) of Patients]
(Page 1 of 2)

Patient Disposition
[Number (%) of Patients]
(Page 2 of 2)

|  | Combination Therapy: Troglitazone/Glyburide | | | | |
|---|---|---|---|---|---|
|  | 200 mg/ 12 mg | 400 mg/ 12 mg | 600 mg/ 12 mg | Glyburide Monotherapy | Total |
| Randomized to Treatment | 78 | 76 | 82 | 79 | 552 |
| Withdrawn Prior to End of Treatment | | | | | |
| Lack of Efficacy | 11 (14.1) | 7 (9.2) | 3 (3.7) | 20 (25.3) | 150 (27.2) |
| Adverse Event | 5 (6.4) | 8 (10.5) | 5 (6.1) | 6 (7.6) | 43 (7.8) |
| Lack of Compliance | 0 (0.0) | 1 (1.3) | 2 (2.4) | 1 (1.3) | 12 (2.2) |
| Pregnancy | 0 (0.0) | 0 (0.0) | 0 (0.0) | 0 (0.0) | 1 (0.2) |
| Other | 6 (7.7) | 6 (7.9) | 2 (2.4) | 6 (7.6) | 28 (5.1) |
| Total | 22 (28.2) | 22 (28.9) | 12 (14.6) | 33 (41.8) | 234 (42.4) |
| Completed Study[a] | 56 (71.8) | 54 (71.1) | 70 (85.4) | 46 (58.2) | 318 (57.6) |

[a]Based on investigator's response on termination case report form

Patients Included in Efficacy Analyses

The number of patients included in the primary efficacy analyses is summarized in Table 7.

RESULTS

Efficacy

Primary Efficacy Parameters: FSG and $HbA_{1c}$

ITT Population Analyses

Mean changes from baseline in FSG and $HbA_1c$ at Week 52 are presented in Table 8. Patients treated with 200 mg/12 mg to 600 mg/12 mg troglitazone/glyburide combination therapy had adjusted mean changes from baseline in FSG of −31.0, −38.0, and −56.4 mg/dL, respectively; these represent mean differences from glyburide of −53.7, −60.8, and −79.1 mg/dL, respectively (all p <0.0001). Patients treated with 400 and 600 mg troglitazone monotherapy showed decreases in FSG compared with glyburide; however, these decreases were not significant.

A similar pattern was observed for $HbA_{1c}$. Patients treated with 200 mg/12 mg to 600 mg/12 mg combination therapy had mean changes from baseline of −0.70%, −0.91%, and −1.75%, respectively; these represent mean differences from glyburide in $HbA_{1c}$ of −1.60%, −1.81%, and −2.65%, respectively (all p <0.0001).

Patients treated with troglitazone monotherapy had increases from baseline in $HbA_{1c}$. The increase was significantly different from glyburide at the 200-mg dose of troglitazone (1.92% compared with 0.90% for glyburide). This may have been attributed to carrying forward data from the patients treated with 200 mg

TABLE 7

Patients Included in Primary Efficacy
Analyses[a] at Week 52
(Number of Patients)

|  | Troglitazone Monotherapy | | | Combination Therapy: Troglitazone/Glyburide | | | Glyburide Monotherapy |
|---|---|---|---|---|---|---|---|
|  | 200 mg | 400 mg | 600 mg | 200 mg/ 12 mg | 400 mg/ 12 mg | 600 mg/ 12 mg | |
| Randomized | 78 | 81 | 78 | 78 | 76 | 82 | 79 |
| No. of Patients in ITT Analysis | 78 | 78 | 76 | 78 | 76 | 80 | 79 |
| Total No. of Patients in the Completer Analysis | 22 | 37 | 34 | 55 | 55 | 70 | 45 |

[a]For FSG troglitazone that withdrew from the study due to lack of efficacy; 55% of patients in this treatment group withdrew due to lack of efficacy.

The decrease from baseline in FSG at the 600-mg/12-mg dose of combination therapy was significantly greater than the decrease at the 200-mg/12-mg dose of combination therapy compared with glyburide (p=0.009). Treatment effects were consistent across centers for the primary parameters.

The mean changes from baseline in FSG and HbA$_{1c}$ at Week 52 are illustrated in FIG. 3.

TABLE 8

Change From Baseline at Month 12 in Primary Glycemic Parameters
ITT Population: Study 991–055
(Page 1 of 2)

| Parameter | Troglitazone Monotherapy | | |
|---|---|---|---|
| | 200 mg | 400 mg | 600 mg |
| Fasting Serum Glucose, mg/dL | | | |
| N | 78 | 78 | 76 |
| Mean Baseline | 226.3 | 212.9 | 230.2 |
| Adjusted Mean Change From Baseline (SE) | 42.4 (7.0) | 20.6 (7.0) | 11.1 (7.1) |
| Adjusted Mean Difference From Glyburide Monotherapy (SE)[a] | 19.6 (9.7) | −2.2 (9.7) | −11.6 (9.7) |
| 95% Confidence Interval[b] | (−5.3, 44.6) | (−27.1, 22.8) | (−36.7, 13.4) |
| Hemoglobin A$_{1c}$, % | | | |
| N | 78 | 79 | 76 |
| Mean Baseline | 9.54 | 9.44 | 9.71 |
| Adjusted Mean Change From Baseline (SE) | 1.92 (0.20) | 0.85 (0.20) | 0.93 (0.20) |
| Adjusted Mean Difference From Glyburide Monotherapy (SE)[a] | 1.02* (0.28) | −0.05 (0.28) | 0.03 (0.28) |
| 95% Confidence Interval[b] | (0.31, 1.74) | (−0.76, 0.66) | (−0.69, 0.75) |

Change From Baseline at Month 12 in Primary Glycemic Parameters
ITT Population: Study 991–055
(Page 2 of 2)

| Parameter | Combination Therapy: Troglitazone/Glyburide | | | Glyburide Monotherapy |
|---|---|---|---|---|
| | 200 mg/12 mg | 400 mg/12 mg | 600 mg/12 mg | |
| Fasting Serum Glucose, mg/dL | | | | |
| N | 78 | 76 | 80 | 79 |
| Mean Baseline | 225.7 | 230.9 | 220.8 | 222.2 |
| Adjusted Mean Change From Baseline (SE) | −31.0 (7.0) | −38.0 (7.1) | −56.4 (6.9) | 22.7 (6.9) |
| Adjusted Mean Difference From Glyburide Monotherapy (SE)[a] | −53.7** (9.7) | −60.8** (9.7) | −79.1** (9.6) | |
| 95% Confidence Interval[b] | (−78.6, −28.9) | (−85.8, −35.7) | (−103.9, −54.4) | |
| Hemoglobin A$_{1c}$, % | | | | |
| N | 78 | 76 | 80 | 79 |
| Mean Baseline | 9.49 | 9.72 | 9.45 | 9.57 |
| Adjusted Mean Change From Baseline (SE) | −0.70 (0.20) | −0.91 (0.20) | −1.75 (0.20) | 0.90 (0.20) |
| Adjusted Mean Difference From Glyburide Monotherapy (SE)[a] | −1.60** (0.28) | −1.81** (0.28) | −2.65* (0.28) | — |
| 95% Confidence Interval[b] | (−2.31, −0.88) | (−2.53, −1.10) | (−2.36, −1.94) | |

[a]ANCOVA with treatment and center effects and baseline as covariate using stepdown test of linear-trend or Bonferroni-Holm adjustment.
[b]95% confidence intervals based on Dunnett's test.
*p ≤ 0.001
**p ≤ 0.0001

FIG. 4 illustrates the mean levels of FSG and $HbA_{1c}$ over time for the ITT population. The majority of improvement in glycemic control (FSG) was observed by the fourth week of therapy.

Completers Analyses

Results of the analysis of the completer population were similar to the results for the ITT population for patients treated with combination therapy (Table 9); patients (completers) treated with all doses of combination therapy had significant reductions (p<0.0001) in FSG and $HbA_{1c}$ compared with glyburide. However, $HbA_{1c}$ decreased significantly (p $\leq$0.05) compared with glyburide monotherapy for patients treated with 400 and 600 mg troglitazone monotherapy; this finding is applicable only to the 44% of patients completing the 1-year study.

TABLE 9

Primary Parameters at Week 52: Completers
(Page 1 of 2)

| Parameter | Troglitazone Monotherapy | | |
|---|---|---|---|
| | 200 mg | 400 mg | 600 mg |
| Hemoglobin $A_{1c}$, % | | | |
| N | 21 | 37 | 34 |
| Mean Baseline (SD) | 9.53 (1.57) | 9.07 (1.61) | 9.35 (1.77) |
| Adjusted Mean Change From Baseline (SE) | 0.55 (0.38) | −0.25 (0.29) | −0.26 (0.30) |
| Adjusted Mean Difference From Glyburide Monotherapy (SE) | −0.23 (0.46) | 1.03* (0.38) | 1.04* (0.39) |
| 95% Confidence Interval[a] | (−1.43 to 0.97) | (−2.02 to −0.04) | (−2.06 to −0.02) |
| Fasting Serum Glucose, mg/dL | | | |
| N | 22 | 37 | 34 |
| Mean Baseline (SD) | 217.5 (44.6) | 196.8 (42.4) | 212.4 (48.9) |
| Adjusted Mean Change From Baseline (SE) | 13.4 (12.0) | −20.5 (9.4) | −11.7 (9.8) |
| Adjusted Mean Difference From Glyburide Monotherapy (SE) | 0.3 (14.6) | −33.6* (12.3) | −24.8 (12.6) |
| 95% Confidence Interval[a] | (−37.61, 38.2) | (−65.5, −1.8) | (−57.5, 7.8) |

Primary Parameters at Week 52: Completers
(Page 2 of 2)

| Parameter | Combination Therapy: Troglitazone/Glyburide | | | Glyburide |
|---|---|---|---|---|
| | 200 mg/12 mg | 400 mg/12 mg | 600 mg/12 mg | Monotherapy |
| Hemoglobin $A_{1c}$, % | | | | |
| N | 55 | 55 | 70 | 45 |
| Mean Baseline (SD) | 9.33 (1.35) | 9.60 (1.32) | 9.35 (1.53) | 9.49 (1.33) |
| Adjusted Mean Change From Baseline (SE) | −0.85 (0.24) | −1.10 (0.24) | −1.96 (0.21) | 0.78 (0.27) |
| Adjusted Mean Difference From Glyburide Monotherapy (SE) | −1.63** (0.35) | −1.88** (0.34) | −2.74** (0.33) | — |
| 95% Confidence Interval[a] | (−2.54 to −0.73) | (−2.77 to −0.99) | (−3.60 to −1.88) | |
| Fasting Serum Glucose, mg/dL | | | | |
| N | 55 | 55 | 70 | 45 |
| Mean Baseline (SD) | 221.7 (55.7) | 224.6 (43.0) | 218.5 (51.1) | 214.7 (34.5) |
| Adjusted Mean Change From Baseline (SE) | −34.1 (7.6) | −46.0 (7.7) | −58.1 (6.8) | 13.1 (8.6) |

TABLE 9-continued

| | | | | |
|---|---|---|---|---|
| Adjusted Mean Difference From Glyburide Monotherapy (SE) | −47.2** (11.2) | −59.1** (11.1) | −71.2** (10.6) | — |
| 95% Confidence Interval[a] | (−76.3, −18.1) | (−87.8, −30.4) | (−98.7, −43.7) | |

[a]ANCOVA (with treatment and center effects and baseline as covariate).
*p ≦ 0.05
**p ≦ 0.0001

Secondary Efficacy Parameters: ITT Population

Total Insulin and C-Peptide

In general, patients treated with troglitazone mono- and combination therapy showed a significant (p≦0.05) decrease in total insulin compared with glyburide at Week 52 (Table 10).

Significant (p≦0.05) decreases in C-peptide were observed for troglitazone monotherapy only (200 and 600 mg troglitazone). It is unclear to what extent these decreases observed are due to the withdrawal of the insulin stimulatory effect associated with sulfonylurea therapy or to a true drug effect (increase in insulin sensitivity). However, decreases in total insulin for combination therapy likely represent a true drug effect (since the insulin stimulatory effect of the sulfonylurea is not removed) and indicate an improvement in insulin sensitivity.

For patients who completed the study (completers), patients treated with 400 and 600 mg troglitazone had decreases in total insulin that were significantly different from glyburide (p<0.05). There were no significant differences in C-peptide from glyburide for any dose of mono- or combination therapy.

TABLE 10

Total Insulin and C-Peptide at Week 52: ITT
(Page 1 of 2)

| | Troglitazone Monotherapy | | |
|---|---|---|---|
| Parameter | 200 mg N = 78 | 400 mg N = 78 | 600 mg N = 76 |
| Total Insulin, μIU/mL | | | |
| Mean Baseline (SD) | 32.3 (30.6) | 33.0 (18.4) | 30.5 (17.7) |
| Adjusted Mean Change From Baseline (SE) | −8.41 (1.39) | −5.90 (1.40) | −11.53 (1.42) |
| Adjusted Mean Difference From Glyburide | −6.96* | −4.44* | −10.07* |
| (95% Confidence Interval) | (−11.96 to −1.96) | (−9.45 to 0.59) | (−15.09 to −5.06) |
| C-Peptide, ng/mL | | | |
| Mean Baseline (SD) | 2.9 (1.1) | 3.1 (1.2) | 3.0 (1.2) |
| Adjusted Mean Change From Baseline (SE) | −0.96 (0.07) | −0.78 (0.07) | −1.01 (0.08) |
| Adjusted Mean Difference From Glyburide | 0.29* | −0.11 | 0.34* |
| (95% Confidence Interval) | (−0.56, −0.02) | (−0.38, 0.16) | (−0.61, −0.07) |

Total Insulin and C-Peptide at Week 52: ITT
(Page 2 of 2)

| | Combination Therapy: Troglitazone/Glyburide | | | Glyburide |
|---|---|---|---|---|
| Parameter | 200 mg/12 mg N = 78 | 400 mg/12 mg N = 76 | 600 mg/12 mg N = 80 | Monotherapy N = 79 |
| Total Insulin, μIU/mL | | | | |
| Mean Baseline (SD) | 28.2 (13.3) | 24.9 (10.6) | 26.4 (13.9) | 27.3 (14.2) |
| Adjusted Mean Change From Baseline (SE) | −3.84 (1.39) | −5.88 (1.42) | −6.08 (1.38) | −1.45 (1.39) |
| Adjusted Mean Difference From Glyburide | −2.39 | −4.43* | −4.63* | — |
| (95% Confidence Interval) | (−7.37 to 2.59) | (−9.45 to 0.58) | (−9.58 to 0.32) | — |
| C-Peptide, ng/mL | | | | |
| Mean Baseline (SD) | 2.8 (1.1) | 2.6 (0.9) | 2.9 (1.1) | 2.7 (0.9) |
| Adjusted Mean Change From Baseline (SE) | −0.75 (0.07) | −0.76 (0.08) | −0.76 (0.07) | −0.67 (0.07) |

TABLE 10-continued

| | | | | |
|---|---|---|---|---|
| Adjusted Mean Difference From Glyburide | −0.08 | −0.09 | −0.09 | — |
| (95% Confidence Interval) | (−0.35, 0.18) | (−0.35, 0.18) | (−0.36, 0.17) | — |

*p ≦ 0.05

$HbA_{1c}$ and Glucose Responders

Table 11 indicates the number of patients who had a ≧30 mg/dL reduction in FSG or a ≧1% reduction in $HbA_{1c}$ (responders) at Week 52. Patients treated with all doses of combination therapy had a significantly higher (p≦0.001) responder rate for $HbA_{1c}$ and FSG compared with glyburide. Sixty-six percent and 64% of patients treated with 600 mg/12 mg combination therapy met the responder criteria for FSG and $HbA_{1c}$, respectively.

TABLE 11

Responders at Week 52: ITT

| | Troglitazone Monotherapy (mg) | | |
|---|---|---|---|
| Responders as Defined by: | 200 N = 78 | 400 N = 78 | 600 N = 76 |
| ≧30 mg/dL Reduction in FSG[a] | | | |
| Responders, N (%) | 11 (14) | 20 (26) | 18 (24) |
| ≧1% Reduction in $HbA_{1c}$[a] | | | |
| Responders, N (%) | 3 (4) | 13 (17) | 8 (11) |

| | Troglitazone/Glyburide (mg) Combination Therapy | | | |
|---|---|---|---|---|
| Responders as Defined by: | 200/12 N = 78 | 400/12 N = 76 | 600/12 N = 80 | Glyburide |
| ≧30 mg/dL Reduction in FSG[a] | | | | |
| Responders, N (%) ≧1% Reduction in $HbA_{1c}$[a] | 37* (47) | 47* (62) | 53* (66) | 10 (13) |
| Responders, N (%) | 29* (37) | 39* (51) | 51* (64) | 4 (5) |

*p ≦ 0.001, significantly different from glyburide (based on step-down CMH tests)
[a]From baseline These improvements in glycemic control are further illustrated by the number of patients who had an $HbA_{1c}$ of ≦8% (FIG. 5). Thirty-three percent, 33%, and 60% of patients treated with 200 mg/12 mg to 600 mg/12 mg combination therapy, respectively, had an $HbA_{1c}$ of ≦8% at the end of the study compared with 10% of glyburide-treated patients. In addition, 22%, 21%, and 41% of patients treated with 200 mg/12 mg to 600 mg/12 mg combination therapy, respectively, had an $HbA_{1c}$ of ≦7% at Week 52 compared with 1% of patients treated with glyburide monotherapy.

Lipid Parameters

Fasting serum lipid profiles were determined at baseline and periodically through Week 52. Apo A1, Apo B, and Lp(a) were determined only at baseline, Month 6, and Month 12 as part of a special laboratory panel. Summary statistics for lipid parameters are shown in Table 12.

Mean triglyceride levels decreased for all therapies with the exception of glyburide, which showed a mean increase at Month 12. Mean decreases were clinically significant for combination therapy, which ranged from −33 to −51 mg/dL (difference from glyburide, −47 to −65 mg/dL), in contrast with glyburide monotherapy, which showed a mean increase in triglycerides of 14 mg/dL.

Mean levels of HDL increased for patients treated with both mono- and combination therapy (0.9–4.5 mg/dL), with the exception of the 400 mg/12 mg combination therapy, which showed a slight decrease. The adjusted mean change from baseline in HDL was significantly greater (p<0.05) than glyburide for patients treated with 600 mg troglitazone monotherapy (difference from glyburide, 4.9 mg/dL).

Mean levels of total cholesterol increased at Month 12 across all treatment groups. Adjusted mean increases were significantly (p<0.05) different from glyburide for all doses of troglitazone (differences from glyburide: 25, 26, and 28 mg/dL for 200, 400, and 600 mg, respectively). Mean LDL also increased across all treatment groups; adjusted mean increases were significantly different (p<0.05) from glyburide for patients treated with 200 mg and 600 mg troglitazone (difference from glyburide: 23 and 19 mg/dL, respectively). There were no clinically or statistically significant changes in VLDL.

There were no statistically significant changes in free fatty acids, Apo A, or Apo B. Lp(a) increased across all treatment groups; the increases in adjusted means were significantly (p<0.05) different from glyburide for patients treated with 400 and 600 mg mono and combination therapy. These increases are not thought to be clinically significant.

Overall, the changes in lipid profiles indicate that troglitazone, either as monotherapy or combination therapy, do not negatively impact atherogenic risk in patients with NIDDM and instead may show a potential clinical benefit.

TABLE 12a

Lipid Parameters at Week 52: ITT Population

| | | Troglitazone Monotherapy | | |
|---|---|---|---|---|
| | Parameter | 200 mg | 400 mg | 600 mg |
| Total Cholesterol, mg/dL | | | | |
| N Baseline | | 78 | 77 | 76 |
| Mean | | 227.97 | 215.77 | 217.45 |

TABLE 12a-continued

Lipid Parameters at Week 52: ITT Population

| | | | |
|---|---|---|---|
| (SD) | (65.04) | (43.03) | (44.50) |
| Median | 216.50 | 208.00 | 210.00 |
| (Min, Max) | (150.0, 663.0) | (120.0, 337.0) | (140.0, 346.0) |
| Change From Baseline | | | |
| Mean | 19.96 | 24.78 | 25.88 |
| (SD) | (58.37) | (45.32) | (46.64) |
| Median | 21.00 | 20.00 | 20.50 |
| (Min, Max) | (−347, 126.0) | (−94.0, 165.0) | (−113, 192.0) |
| LDL Cholesterol, mg/dL | | | |
| N | 78 | 77 | 76 |
| Baseline | | | |
| Mean | 137.33 | 129.32 | 131.43 |
| (SD) | (39.07) | (31.42) | (38.20) |
| Median | 132.00 | 129.00 | 130.50 |
| (Min, Max) | (65.0, 243.0) | (47.0, 221.0) | (50.0, 240.0) |
| Change From Baseline | | | |
| Mean | 17.78 | 12.09 | 16.21 |
| (SD) | (41.17) | (31.49) | (34.29) |
| Median | 20.50 | 11.00 | 15.00 |
| (Min, Max) | (−149, 132.0) | (−95.0, 89.0) | (−71.0, 88.0) |

| | Combination Therapy: Troglitazone/Glyburide | | | |
|---|---|---|---|---|
| Parameter | 200 mg/12 mg | 400 mg/12 mg | 600 mg/12 mg | Glynase |
| Total Cholesterol, mg/dL | | | | |
| N | 78 | 76 | 79 | 78 |
| Baseline | | | | |
| Mean | 208.97 | 218.00 | 212.71 | 215.50 |
| (SD) | | (45.15) | (41.71) | (39.94) |
| Median | 205.50 | 218.50 | 209.00 | 209.00 |
| (Min, Max) | (106.0, 380.0) | (133.0, 305.0) | (134.0, 356.0) | (131.0, 326.0) |
| Change From Baseline | | | | |
| Mean | 15.55 | 7.71 | 11.58 | 6.17 |
| (SD) | (34.34) | (39.09) | (42.95) | (36.74) |
| Median | 17.00 | 13.50 | 4.00 | 6.50 |
| (Min, Max) | (−73.0, 96.0) | (−85.0, 161.0) | (−91.0, 140.0) | (−113.0, 122.0) |
| LDL Cholesterol, mg/dL | | | | |
| N | 78 | 76 | 79 | 78 |
| Baseline | | | | |
| Mean | 117.53 | 126.87 | 121.80 | 132.27 |
| (SD) | (37.84) | (30.75) | (33.16) | (31.51) |
| Median | 117.00 | 126.50 | 119.0 | 131.00 |
| (Min, Max) | (3.0, 240.0) | (49.0, 217.0) | (54.0, 215.0) | (70.0, 212.0) |
| Change From Baseline | | | | |
| Mean | 14.74 | 8.63 | 12.70 | 3.49 |
| (SD) | (36.33) | (31.75) | (33.39) | (27.83) |
| Median | 13.50 | 8.50 | 14.00 | 4.00 |
| (Min, Max) | (−69.0, 130.0) | (−66.0, 131.0) | (−66.0, 121.0) | (−60.0, 84.0) |

TABLE 12b

Lipid Parameters at Week 52: ITT Population
(Page 1 to 2)

| | Troglitazone Monotherapy | | |
|---|---|---|---|
| Parameter | 200 mg | 400 mg | 600 mg |
| VLDL Cholesterol, mg/dL | | | |
| N | 78 | 77 | 76 |

TABLE 12b-continued

| Baseline | | | |
|---|---|---|---|
| Mean | 48.49 | 44.27 | 54.67 |
| (SD) | (31.05) | (26.94) | (40.67) |
| Median | 42.50 | 39.00 | 44.00 |
| (Min, Max) | (8.0, 170.0) | (3.0, 152.0) | (16.0, 243.0) |
| Change From Baseline | | | |
| Mean | 3.54 | 8.48 | −0.36 |
| (SD) | (26.20) | (34.65) | (46.41) |
| Median | 3.50 | 3.00 | −3.00 |
| (Min, Max) | (−8.10, 104.0) | (−47.0, 168.0) | (−145, 223.0) |
| HDL Cholesterol, mg/dL | | | |
| N | 78 | 77 | 76 |
| Baseline | | | |
| Mean | 36.87 | 37.73 | 37.68 |
| (SD) | (8.97) | (16.24) | (17.75) |
| Median | 35.50 | 36.00 | 35.00 |
| (Min, Max) | (21.0, 70.0) | (14.0, 144.0) | (16.0, 158.0) |
| Change From Baseline | | | |
| Mean | 0.86 | 2.99 | 4.53 |
| (SD) | (6.72) | (14.98) | (24.83) |
| Median | 1.00 | 3.00 | 3.00 |
| (Min, Max) | (−18.0, 19.0) | (−94.0, 66.0) | (−112, 160.0) |

Lipid Parameters at Week 52: ITT Population
(Page 2 of 2)

| | Combination Therapy: Troglitazone/Glyburide | | | Glyburide |
|---|---|---|---|---|
| Parameter | 200 mg/12 mg | 400 mg/12 mg | 600 mg/12 mg | Monotherapy |
| VLDL Cholesterol, mg/dL | | | | |
| N | 78 | 76 | 79 | 78 |
| Baseline | | | | |
| Mean | 51.06 | 54.51 | 51.42 | 46.81 |
| (SD) | (41.61) | (34.10) | (37.56) | (33.35) |
| Median | 41.50 | 46.00 | 39.00 | 38.00 |
| (Min, Max) | (5.0, 285.0) | (7.0, 191.0) | (3.0, 239.0) | (9.0, 197.0) |
| Change From Baseline | | | | |
| Mean | 3.36 | −4.47 | −4.01 | −2.78 |
| (SD) | (23.93) | (30.71) | (29.14) | (27.77) |
| Median | 2.00 | −3.00 | −3.00 | −1.00 |
| (Min, Max) | (−96.0, 58.0) | (−138, 90.0) | (−80.0, 69.0) | (−133, 127.0) |
| HDL Cholesterol, mg/dL | | | | |
| N | 78 | 76 | 79 | 78 |
| Baseline | | | | |
| Mean | 36.63 | 38.34 | 35.01 | 35.71 |
| (SD) | (11.63) | (18.74) | (11.60) | (7.37) |
| Median | 34.50 | 35.00 | 33.00 | 35.00 |
| (Min, Max) | (17.0, 100.0) | (22.0, 146.0) | (18.0, 110.0) | (18.0, 58.0) |
| Change From Baseline | | | | |
| Mean | 1.67 | −1.76 | 4.47 | −0.15 |
| (SD) | (14.35) | (18.99) | (15.75) | (5.97) |
| Median | 1.00 | −0.50 | 3.00 | −1.00 |
| (Min, Max) | (−70.0, 90.0) | (−122, 17.0) | (−82.0, 81.0) | (−13.0, 20.0) |

TABLE 12c

| Lipid Parameters at Week 52: ITT Population (Page 1 to 2) | | | |
|---|---|---|---|
| | Troglitazone Monotherapy | | |
| | 200 mg | 400 mg | 600 mg |
| Triglycerides, mg/dL | | | |
| N | 78 | 77 | 76 |
| Baseline | | | |
| Mean | 275.54 | 273.21 | 279.76 |
| (SD) | (459.17) | (327.86) | (239.93) |
| Median | 201.50 | 198.00 | 212.00 |
| (Min, Max) | (74.0, 4120) | (47.0, 2770) | (83.0, 1741) |
| Change From Baseline | | | |
| Mean | −35.77 | −3.86 | −9.59 |
| (SD) | (414.77) | (333.10) | (307.28) |
| Median | 3.50 | −2.00 | −24.00 |
| (Min, Max) | (−3514, 365.0) | (−2281, 1062) | (−1027, 2186) |
| Free Fatty Acids, mEq/L | | | |
| N | 78 | 78 | 76 |
| Baseline | | | |
| Mean | 0.74 | 0.86 | 0.81 |
| (SD) | (0.33) | (0.50) | (0.84) |
| Median | 0.68 | 0.78 | 0.73 |
| (Min, Max) | (0.1, 2.3) | (0.3, 3.6) | (0.3, 7.7) |
| Change From Baseline | | | |
| Mean | −0.09 | −0.17 | −0.19 |
| (SD) | (0.33) | (0.54) | (0.89) |
| Median | −0.04 | −0.12 | −0.11 |
| (Min, Max) | (−1.7, 0.6) | (−3.0, 0.8) | (−7.4, 1.1) |

| Lipid Parameters at Week 52: ITT Population (Page 2 of 2) | | | | |
|---|---|---|---|---|
| | Combination Therapy: Troglitazone/Glyburide | | | Glyburide |
| Parameter | 200 mg/12 mg | 400 mg/12 mg | 600 mg/12 mg | Monotherapy |
| Triglycerides, mg/dL | | | | |
| N | 78 | 76 | 79 | 78 |
| Baseline | | | | |
| Mean | 284.19 | 265.78 | 251.71 | 223.40 |
| (SD) | (383.59) | (185.17) | (205.06) | (156.11) |
| Median | 194.50 | 218.00 | 198.00 | 176.50 |
| (Min, Max) | (55.0, 3215) | (56.0, 1129) | (39.0, 1594) | (53.0, 831.0) |
| Change From Baseline | | | | |
| Mean | −32.86 | −37.33 | −50.46 | 14.24 |
| (SD) | (248.21) | (149.09) | (177.90) | (145.74) |
| Median | −3.00 | −15.00 | −39.00 | 8.00 |
| (Min, Max) | (−1795, 487.0) | (−890, 388.0) | (−1091, 618.0) | (−467, 831.0) |
| Free Fatty Acids, mEq/L | | | | |
| N | 78 | 76 | 80 | 79 |
| Baseline | | | | |
| Mean | 0.72 | 0.79 | 0.70 | 0.76 |
| (SD) | (0.38) | (0.40) | (0.23) | (0.49) |
| Median | 0.66 | 0.72 | 0.66 | 0.68 |
| (Min, Max) | (0.3, 2.7) | (0.3, 3.0) | (0.2, 1.4) | (0.3, 3.8) |
| Change From Baseline | | | | |
| Mean | −0.12 | −0.15 | −0.08 | −0.05 |
| (SD) | (0.36) | (0.37) | (0.26) | (0.51) |
| Median | −0.10 | −0.12 | −0.09 | 0.03 |
| (Min, Max) | (−1.3, 0.8) | (−2.2, 0.9) | (−0.5, 0.6) | (−3.5, 0.9) |

TABLE 12d

| | Lipid Parameters at Week 52: ITT Population (Page 1 to 2) | | |
|---|---|---|---|
| | Troglitazone Monotherapy | | |
| Parameter | 200 mg | 400 mg | 600 mg |
| Apo A1[a], mg/dL | | | |
| N | 22 | 37 | 35 |
| Baseline | | | |
| Mean | 143.9 | 138.6 | 138.3 |
| (SD) | (20.4) | (23.6) | (24.8) |
| Median | (108, 190) | (103.5, 203.0) | (94.5, 197.0) |
| (Min, Max) | | | |
| Change From Baseline | | | |
| Mean | 1.9 | −1.5 | −1.9 |
| (SD) | (14.2) | (15.4) | (21.1) |
| Median | (−21.5, 26.5) | (−53.0, 40.0) | (−54.5, 57.5) |
| (Min, Max) | | | |
| Apo B[a], mg/dL | | | |
| N | 22 | 37 | 35 |
| Baseline | | | |
| Mean | 134.9 | 124.2 | 118.2 |
| (SD) | (31.8) | (28.4) | (30.0) |
| Median | (94.0, 209.5) | (77.5, 198.5) | (68.0, 199.5) |
| (Min, Max) | | | |
| Change From Baseline | | | |
| Mean | 6.4 | 3.4 | 3.1 |
| (SD) | (29.0) | (35.5) | (37.9) |
| Median | (−55.0, 59.5) | (−99.0, 121.5) | (−60.5, 172.0) |
| (Min, Max) | | | |

| | Lipid Parameters at Week 52: ITT Population (Page 2 of 2) | | | |
|---|---|---|---|---|
| | Combination Therapy: Troglitazone/Glyburide | | | Glyburide |
| Parameter | 200 mg/12 mg | 400 mg/12 mg | 600 mg/12 mg | Monotherapy |
| Apo A1[a], mg/dL | | | | |
| N | 56 | 56 | 70 | 47 |
| Baseline | | | | |
| Mean | 142.4 | 140.1 | 138.1 | 141.5 |
| (SD) | (23.7) | (21.4) | (22.3) | (20.8) |
| Median | (90.0, 211.0) | (83.5, 198.0) | (93.5, 212.0) | (108, 208) |
| (Min, Max) | | | | |
| Change From Baseline | | | | |
| Mean | −1.2 | −4.8 | −4.9 | −1.1 |
| (SD) | (18.5) | (20.7) | (14.1) | (14.2) |
| Median | (−44.0, 67.5) | (−60.0, 89.0) | (−33.5, 38.0) | (−53.5, 38.0) |
| (Min, Max) | | | | |
| Apo B[a], mg/dL | | | | |
| N | 56 | 56 | 70 | 47 |
| Baseline | | | | |
| Mean | 117.4 | 123.5 | 117.6 | 124.5 |
| (SD) | (26.7) | (25.3) | (23.7) | (21.5) |
| Median | (68.0, 211.0) | (80.5, 181.5) | (67.0, 190.5) | (85.0, 166.0) |
| (Min, Max) | | | | |
| Change From Baseline | | | | |
| Mean | 6.3 | 0.1 | −0.7 | 2.9 |
| (SD) | (20.4) | (23.3) | (21.7) | (23.0) |
| Median | (−42.5, 85.5) | (−66.0, 58.0) | (−55.5, 66.0) | (−52.5, 101.5) |
| (Min, Max) | | | | |

TABLE 12e

Lipid Parameters at Week 52: ITT Population
(Page 1 of 2)

|  | Troglitazone Monotherapy | | |
|---|---|---|---|
| Parameter | 200 mg | 400 mg | 600 mg |
| LP(a)[a], mg/dL | | | |
| N | 22 | 37 | 35 |
| Baseline | | | |
| Mean | 23.4 | 24.1 | 14.3 |
| (SD) | (21.7) | (24.9) | (19.4) |
| Median | (0.8, 82.5) | (0.8, 76.5) | (0.8, 84.0) |
| (Min, Max) | | | |
| Change From Baseline | | | |
| Mean | 8.8 | 10.0 | 9.1 |
| (SD) | (13.2) | (12.0) | (11.7) |
| Median | (−10.0, 38.0) | (−9.5, 33.5) | (−8.0, 36.5) |
| (Min, Max) | | | |

Mean Lipid Parameters at Week 52: ITT Population
(Page 1 of 2)

|  | Combination Therapy: Troglitazone/Glyburide | | | Glyburide |
|---|---|---|---|---|
| Parameter | 200 mg/12 mg | 400 mg/12 mg | 600 mg/12 mg | Monotherapy |
| LP(a)[a], mg/dL | | | | |
| N | 56 | 56 | 70 | 47 |
| Baseline | | | | |
| Mean | 25.4 | 22.4 | 16.8 | 16.5 |
| (SD) | (29.0) | (27.5) | (23.0) | (19.9) |
| Median | (0.8, 131.0) | (0.8, 131.0) | (0.8, 134.5) | (0.8, 94.5) |
| (Min, Max) | | | | |
| Change From Baseline | | | | |
| Mean | 7.0 | 10.7 | 10.4 | 1.4 |
| (SD) | (12.5) | (18.0) | (18.1) | (11.3) |
| Median | (−28.5, 46.5) | (−5.0, 75.5) | (−33.0, 95.1) | (−13.0, 68.5) |
| (Min, Max) | | | | |

Blood Pressure

In general, patients included in this study were not hypertensive; the mean blood pressure (BP) for the study population was approximately 129/78 mm Hg. Patients treated with 600 mg/12 mg combination therapy had a significant decrease in mean diastolic BP (p<0.05) compared with glyburide monotherapy (decrease of −2.6 mm Hg compared to glyburide).

Meal Tolerance Testing

Meal tolerance testing was performed in a subset of patients at baseline and at Months 6 and 12. Postprandial glucose, insulin, and C-peptide levels were determined at 30, 60, 90, and 120 minutes after a standard meal (Sustacal HC) (Table 13).

At Month 12, the mean glucose AUC(0–2 hr) decreased significantly (p ≦0.05) compared with glyburide for patients treated with all dose levels of troglitazone/glyburide combination therapy and 600 mg troglitazone monotherapy. All doses of monotherapy and combination therapy showed decreases in insulin and C-peptide AUC(0–2 hr); however, none of these decreases reached statistical significance.

TABLE 13

Mean Change From Baseline[a] in AUC (0–2 hrs) 2 Hours After
Standard Meal at Month 12: Completers

|  | Troglitazone Monotherapy | | |
|---|---|---|---|
| Parameter | 200 mg<br>N = 8 | 400 mg<br>N = 8 | 600 mg<br>N = 11 |
| Glucose AUC (0–2 hr), mg/dL · hr | | | |
| Baseline (SD) | 574 (104) | 568 (103) | 558 (97) |
| Change From Baseline at Month 12 (SD) | 5 (97) | 37 (170) | −137* (123) |

TABLE 13-continued

Mean Change From Baseline[a] in AUC (0–2 hrs) 2 Hours After Standard Meal at Month 12: Completers

| Total Insulin AUC (0–2 hr), µ1U/mL · hr | | | |
|---|---|---|---|
| Baseline (SD) | 154.6 (110.0) | 140.8 (69.0) | 171.0 (72.3) |
| Change From Baseline at Month 12 (SD) | −46.7 (27.1) | −54.1 (55.3) | −65.5 (44.6) |
| C-Peptide AUC (0–2 hr), ng/mL · hr | | | |
| Baseline (SD) | 8.3 (3.9) | 9.7 (3.4) | 10.4 (3.7) |
| Change From Baseline at Month 12 (SD) | −2.2 (1.9) | −4.2 (2.7) | −3.1 (3.0) |

| | Combination Therapy:Troglitazone/Glyburide | | | Glyburide |
| Parameter | 200 mg/12 mg N = 13 | 400 mg/12 mg N = 13 | 600 mg/12 mg N = 15 | Monotherapy N = 12 |
|---|---|---|---|---|
| Glucose AUC (0–2 hr), mg/dL · hr | | | | |
| Baseline (SD) | 629 (156) | 598 (72) | 583 (110) | 582 (77) |
| Change From Baseline at Month 12 (SD) | −155* (183) | −114* (103) | −94* (138) | 35 (88) |
| Total Insulin AUC (0–2 hr), µ1U/mL · hr | | | | |
| Baseline (SD) | 148.9 (66.5) | 123.2 (51.4) | 133.7 (75.1) | 124.2 (45.3) |
| Change From Baseline at Month 12 (SD) | −39.7 (40.1) | −25.1 (37.3) | −27.1 (56.6) | −21.7 (28.6) |
| C-Peptide AUC (0–2 hr), ng/mL · hr | | | | |
| Baseline (SD) | 10.0 (4.5) | 9.8 (5.2) | 10.1 (2.9) | 8.8 (2.7) |
| Change From Baseline at Month 12 (SD) | −3.7 (3.0) | −3.8 (3.4) | −2.9 (2.4) | −2.3 (2.6) |

[a]Negative change from baseline indicates improvement
*p ≦ 0.05, based on ANCOVA including effects for center, treatment, and baseline as a covariate. Adjusted mean changes are presented in Appendix D.5.

Weight

Statistically significant (p ≦ 0.0001) increases in mean body weight (6–13 lbs) occurred in patients treated with all doses of combination therapy compared with glyburide (Table 14); patients treated with glyburide monotherapy showed a mean weight loss of 1 lb. Patients treated with troglitazone monotherapy showed mean decreases from baseline of 1 to 7 lbs. This increase in weight for patients on combination therapy is possibly a result of improved glycemic control, decreased glycosuria, or a potentiation of the known effect of sulfonylurea therapy on weight gain.

TABLE 14

Mean Change From Baseline in Body Weight at Month 12: ITT
(Page 1 of 2)

| | Troglitazone Monotherapy (mg) | | |
|---|---|---|---|
| | 200 N = 79 | 400 N = 78 | 600 N = 76 |
| Mean Baseline (SD) | 201.7 (42.0) | 216.6 (54.8) | 207.1 (46.1) |
| Adjusted Mean Change (SE) | −6.9 (1.2) | −3.9 (1.2) | −0.8 (1.2) |
| Difference From Glyburide (SE) | −5.6* (1.6) | −2.6 (1.6) | 0.5 (1.6) |

Mean Change From Baseline in Body weight at Month 12: ITT

| | Troglitazone/Glyburide (mg) Combination Therapy | | | |
|---|---|---|---|---|
| | 200/12 N = 77 | 400/12 N = 75 | 600/12 N = 79 | Glyburide N = 79 |
| Mean Baseline (SD) | 202.5 (35.8) | 200.6 (42.4) | 196.2 (43.2) | 196.2 (43) |
| Adjusted Mean Change (SE) | 5.8 (1.2) | 7.7 (1.2) | 13.1 (1.2) | −1.3 (1.2) |
| Difference From Glyburide (SE) | 7.1** (1.6) | 9.0** (1.6) | 14.4** (1.6) | — — |

*p ≦ 0.05.
**p ≦ 0.0001.

Diabetes Symptoms Assessment

Ten common symptoms of diabetes, including fatigue, frequent urination, and thirst, were assessed for severity (0=absent, 1=mild, 2=moderate, 3=severe) at baseline and monthly throughout the study. Mean baseline scores were generally below one for all 10 symptoms and mean scores remained below one at the end of the study.

Pharmacokinetic Analysis: Plasma Trough Concentrations of Troglitazone

Individual trough plasma troglitazone concentrations are shown in Appendix E. Mean trough plasma concentrations of troglitazone at Week 12 are summarized in Table 15.

Clinical Laboratory Measurements

Changes From Baseline to Outside Normal Range

Baseline clinical laboratory parameters were compared with values at the end of the study (last visit) to identify any abnormal trends. The percent of patients with increases or decreases in laboratory values were calculated based on the number of patients at risk for changes outside of the refer-

TABLE 15

Mean (% RSD) Trough Plasma Concentrations (ng/mL) of Troglitazone at Week 12

| Troglitazone 200 mg QD (N = 48) | Troglitazone 200 mg QD + Glyburide (N = 76) | Troglitazone 400 mg QD (N = 54) | Troglitazone 400 mg QD + Glyburide (N = 70) | Troglitazone 600 mg QD (N = 61) | Troglitazone 600 mg QD + Glyburide (N = 77) |
|---|---|---|---|---|---|
| 145 (150%) | 111 (70%) | 238 (76%) | 181 (70%) | 285 (86%) | 291 (93%) |

Variability in trough plasma troglitazone concentrations was high as reflected by the large %RSD values. Mean trough troglitazone concentrations generally increased with increasing troglitazone doses. The trough concentrations obtained in this study using troglitazone tablets from Lots CM 1581194 and CM 0120295 were similar to those observed in the corresponding dose groups in a dose-proportionality study using troglitazone tablets from Lot CM 1581194. For each troglitazone dose group, mean trough plasma troglitazone concentrations for the troglitazone monotherapy appeared similar to those for troglitazone/glyburide combination therapy. This is consistent with the results of a study indicating a lack of pharmacokinetic interaction between glyburide and troglitazone.

Safety

Adverse Events

Adverse events that were treatment emergent (not present at baseline) are summarized in the following section using a modified COSTART dictionary. If, however, an adverse event present at baseline increased in intensity or frequency during treatment, the event was included in the summaries. Each patient reporting an adverse event was counted only once for that event regardless of the number of times the adverse event was reported. Associated adverse events were those considered by the investigator to be possibly, probably, or definitely related to study therapy.

Overview

Troglitazone monotherapy and troglitazone/glyburide combination therapy were well-tolerated throughout the study. Overall, 70% of patients treated with troglitazone monotherapy had adverse events compared with 90% of patients treated with glyburide (control) therapy. Patients treated with combination therapy had an incidence of adverse events similar to glyburide therapy, 91%. To what extent the high dropout rate for troglitazone monotherapy affected the incidence of adverse events is not known.

In general, the incidence of adverse events was not influenced by age or menopausal status. Overall, patients treated with combination therapy had a higher incidence of associated adverse events (26%) compared with those treated with glyburide (10%).

The incidence of serious adverse events was similar across all treatments; the percent of patients withdrawn for adverse events was 8% across treatments.

ence range; i.e., patients with low or high values at baseline were not considered at risk for a decrease or increase, respectively.

No clinically adverse trends were noted in any laboratory parameter. However, dramatic improvement (i.e., decreases) in urine glucose for all combination therapy groups was evident.

Clinically Important Changes

The Guidelines for Evaluation of Clinical Laboratory Values were used to identify those patients that may have had a clinically important change in one or more laboratory values at any point during the study. Laboratory results were then reviewed for these particular patients to determine which patients actually had clinically important changes in a given laboratory parameter. Minimal changes occurred within any laboratory parameter across all treatments.

Patients meeting criteria for clinically important changes are discussed below. A greater number of patients treated with troglitazone combination therapy than troglitazone monotherapy had laboratory changes meeting clinically meaningful change criteria. One patient had significantly elevated ALT and AST which was considered attributable to study drug by the investigator and which causality cannot be confidently ruled out: Patient 4, Center 16, experienced significantly elevated ALT (1155 U/L) and AST (458 U/L) following 57 days of troglitazone 600 mg combination therapy and receiving a flu vaccine. ALT and AST returned to baseline levels 49 days after therapy was withdrawn.

Specific Laboratory Parameters

Hematology:

Minimal changes occurred with any of the hematological parameters. Changes that met criteria for possible clinical importance were increases or decreases within the normal range or transient changes that subsequently resolved. Patients meeting clinically important changes in hematology parameters are noted here. Thirty-four patients had changes in hemoglobin or hematocrit or both meeting criteria for clinically meaningful change. Seven patients had mildly transient decreases which returned to baseline levels while remaining on troglitazone (3 patients; two on 400 mg, one on 600 mg) or troglitazone combination (4 patients; three on 400 mg/12 mg, one on 600 mg/12 mg). Eight patients had slight decreases within the normal range or were near the lower normal limit at baseline and dropped below normal limits during the study, and hemoglobin or hematocrit levels remained stable throughout the study. Eight patients had levels below normal reference limits for hemoglobin or hematocrit at baseline and remained below normal limits throughout the study, none were withdrawn for this reason. Fourteen patients had decreases in hemoglobin and hematocrit secondary to blood loss for several reasons, e.g., acute bleeding due to automobile accident, rectal bleeding due to hemorrhoids, donated blood, bleeding ulcer (2 patients), CABG surgery (4 patients). Two of these patients were consuming up to 50 concurrent medications and two additional patients had severe infections associated temporally with decreased hemoglobin and hematocrit. After thorough review of patient laboratory data, no patient experienced clinically important decreases in any hematological parameter that can be directly attributable to troglitazone.

Liver Enzymes:

Thirteen patients had clinically meaningful elevations in ALT, AST, or both. Three of these patients were terminated due to enzymes elevations; all were followed and enzymes returned to either baseline or within normal limits. Four additional patients had transient elevations which resolved while remaining on troglitazone or troglitazone combination. Two patients on troglitazone 600 mg combination, three on troglitazone 300 mg combination, and one patient on troglitazone 200 mg monotherapy had mildly elevated (<3×upper normal limit) at the end of the study. Three of these patients were concomitantly using many additional medications for concurrent illness which cannot be ruled out as causal or contributory to their elevated enzymes.

DISCUSSION

Although glitazones (e.g., troglitazone) enhance insulin action at the cellular level, they do not stimulate insulin release, nor do they mimic its action. The therapeutic benefits of glitazone treatment depends on the availability of adequate amounts of insulin. The addition of a glitazone to concurrent sulfonylurea treatment provides a balance of stimulated release of insulin while ameliorating insulin resistance. The results obtained in this study provide evidence of significant and synergistic improvement in glycemic control of patients with very few remaining therapeutic options.

Glycemic Parameters

The mean change from baseline in FSG for the 600T/12G arm was −56 mg/dL, representing a difference of −79 mg/dL from the control arm. The improvement in FSG is confirmed by a mean change from baseline in $HbA_{1c}$ of −1.75% in the same treatment arm, a difference of −2.65% from the active control arm. Approximately 60% of patients in the 600T/12g arm reached an $HbA_{1c}$ level ≦8%. The magnitude of these changes represent an impressive improvement in glycemic control without the use of exogenous insulin. Although the glycemic improvements observed in the 400T/12G and the 200T/12G arms were less pronounced, these data provide the rationale for titration based on the level of glycemic control.

The results of the troglitazone monotherapy treatment arms, on the other hand, should be interpreted carefully. Considering the slow acting properties of troglitazone, an immediate switch from sulfonylurea to troglitazone would cause a deterioration in glycemic control before any improvement is observed. Moreover, the immediate switch in patients who are already in poor control would worsen the degree of glucose toxicity and make adequate glycemic control even harder to achieve. This situation was observed in the monotherapy arms. Those patients were switched from the maximum dose of glyburide to troglitazone monotherapy at the time of randomization. Consequently, glycemic control in the majority of patients worsened, and patients with excessive hyperglycemia were withdrawn from the study for safety purposes. Due to the nature of the ITT analysis with LOCF, the average change in FSG and $HbA_{1c}$ is reflective of the high glycemic values of patients who discontinued early. In other words, the higher the early dropout rate, the worse the end of study results would appear. This is especially the case in the T200 arm since the dropout rate due to lack of efficacy reached almost 60%. Therefore, the results of the ITT analysis in this case are not a good reflection of the true response of all patients. On the other hand, the results of the completers analysis represent a bias in favor of troglitazone. The completers analysis would effectively select the sub-population who are more likely to respond to study medication. The true response of these treatment arms is more likely to lie somewhere between the results of the ITT and completers populations. Nevertheless, the clinical interpretation of these data indicates that switching patients from sulfonylurea use, particularly those on high doses, to troglitazone monotherapy is not an appropriate therapeutic approach.

Troglitazone should be added to current treatment regimens of a sulfonylurea beginning at 200 mg and increasing up to 600 mg as needed to optimize glycemic control. As patients reach target goals of glycemic control, the dose of sulfonylurea may be reduced or even eliminated based on the level of glycemic control. Hence, in these patients (sulfonylurea failures), troglitazone as monotherapy is achieved only if warranted based upon glycemic control parameters. Faced with the alternative of reducing the dosage of one of the agents, the pathophysiology of the disease should be considered. Treating the basic defect of Type II diabetes, i.e., insulin resistance, should take precedence over exhausting pancreatic insulin secretion by sulfonylurea stimulation. Therefore, as glycemic control improves the sulfonylurea should be considered for dose reduction or even discontinuation if indicated. Troglitazone alone can be effective in naive patients who are not well-controlled on diet and exercise but have not been managed on oral agents. The deficit in the insulin secretory capacity of naive patients is generally relative, and the improvement in insulin sensitivity may be sufficient to restore normoglycemia.

Insulin, C-peptide, and Meal Tolerance Test

The insulin reduction observed in the combination treatment arms reflects an improvement in insulin sensitivity since the lower insulin level is associated with significant decreases in FSG and $HbA_{1c}$ rather than increases. The direction of the change in the fasting levels of insulin and serum glucose is mirrored by similar changes in the AUC of the insulin and serum glucose during the meal tolerance test for the combination arms. The improved insulin sensitivity leads to a reduced demand on pancreatic secretion of insulin, a desirable outcome given the natural progression of the disease.

The magnitude of the reduction in insulin in the monotherapy arms is greater than that observed in the various combination arms. While a similar reduction between the monotherapy and the combination treatment arms would have been expected based upon enhanced insulin activity, the additional decrease in insulin levels may be attributed to the removal of sulfonylurea-stimulated insulin secretion. Finally, the reduction observed in the control arm (micronized glyburide) may be attributed to gradual degradation of the pancreatic secretory function or secondary failure typically observed with sulfonylurea treatment over time. This change cannot be attributed to improvements in insulin sensitivity, since FSG levels increased and did not decrease. The observed changes in insulin levels were confirmed by similar changes in direction and magnitude in C-peptide levels for all treatment arms.

Lipid Parameters

The classical manifestations of insulin resistance in a diabetic population are elevated triglycerides and low levels of HDL. Therefore, the reversal of insulin resistance should be expected to elicit favorable changes in these lipid parameters, as observed in this study. Although statistical significance was reached in some (but not all) treatment arms, the general trend of the changes is consistent with the reversal of insulin resistance, i.e., a reduction in triglycerides and an increase in HDL. The reduction in insulin levels and resultant increase in lipoprotein lipase (LPL) activity could be responsible for the triglyceride and HDL changes. Modest increases of minimal clinical significance in total cholesterol and LDL were observed in the monotherapy arms. Similar, but less pronounced changes were observed in the combination arms. It is important to note that LDL levels were measured directly and not calculated indirectly from triglycerides and cholesterol levels using the Freidwald formula. Both LDL and cholesterol are relatively constant parameters and are not affected by the fasting state of the patient. Triglycerides, however, are extremely variable, and affected by the fasting state of the patient. This variability could explain the fact that a clinically desirable mean reduction in excess of 50 mg/dL observed in the T600/G12 group did not reach statistical significance. In contrast, the magnitude of change in both cholesterol and LDL was of little clinical significance (only 4%–7% in the combination treatment arms) but was statistically significant.

Lipid changes observed in this study are consistent with results from prior studies. The favorable change in triglycerides, HDL, and FFA are contrasted by minimal increases in total cholesterol, LDL, Lp(a), and no changes in Apo (A1) and Apo (B). Collectively, these changes may be interpreted as having a potentially beneficial impact on atherogenic risk. It should be noted that patients with elevated triglycerides levels could potentially benefit from troglitazone treatment and provide synergism to the management of their dyslipidemia since elevated triglyceride levels are recognized as an independent risk factor for cardiovascular disease.

Blood Pressure

No statistically or clinically significant changes were observed in systolic blood pressure at the end of the study. Mean diastolic blood pressure, however, decreased significantly ($p<0.05$) for patients treated with 600 mg/12 mg combination therapy. A reduction in diastolic BP is consistent with similar observation in other troglitazone studies. The direction and magnitude of the DBP change offers a clinically desirable endpoint in this population. Given the fact that hypertensive patients were excluded from this study, only minor changes would be expected. Since this study was not powered to detect small changes in blood pressure, the direction of the observed change still represents a desirable change in this population. The reduction in diastolic BP is corroborated by a decrease in the calculated peripheral resistance in the subgroup of patients that underwent cardiac output measurements in this study. This change in BP could result indirectly from reversing insulin resistance and amelioration of hyperinsulinemia, or alternatively, from a direct action of troglitazone on peripheral vasculature.

Weight

A statistically significant increase in weight was observed in the combination arms in contrast to the troglitazone monotherapy arms in which modest weight losses of 1 to 7 lbs were seen. While the magnitude of the change is relatively small (approximately 6%), minor increases in weight in this population should be carefully monitored. The fact that weight increases were observed in the combination therapy arms only and not the monotherapy arms is suggestive of factors other than troglitazone therapy being responsible for weight increases. Several factors may have contributed to weight gain in this study. The fact that weight gain was mainly observed in treatment arms associated with improved glycemic control suggests that diminished glycosuria may be contributing to weight gain. The weight increase may possibly be a result of potentiation of the known affect of sulfonylurea therapy on weight gain. In addition, patients in this study were instructed on a weight maintenance diet for the duration of the study. Appropriate diabetic diet instructions targeting ideal body weight was not implemented in this study. Finally, improving hyperglycemia and achieving target glycemic control in this population is a disincentive to maintain strict caloric and sugar intake. In clinical practice, diet and exercise should be strongly emphasized to avoid potential weight gain.

Safety

Troglitazone, both as mono- and combination therapy, was well-tolerated during the study. The overall adverse event profile of troglitazone/glyburide combination therapy was similar to the adverse event profile of glyburide monotherapy. Most adverse events occurred at the lower incidence in patients treated with troglitazone monotherapy compared with the patients treated with glyburide monotherapy. This may be attributed to a better adverse event profile for troglitazone and may in part be due to the high dropout rate for patients treated with troglitazone monotherapy. Tolerance was also evident by the rare occurrence of unacceptable levels of clinical laboratory parameters; most of these occurrences resolved while study treatment continued.

Summary

In summary, patients with Type II diabetes receiving maximum doses of sulfonylurea have very few oral therapeutic options remaining. Aside from insulin resistance, the hallmark of the disease at this stage is mainly a diminished pancreatic response to glucose stimulus. Improving insulin resistance is of great benefit when added to a current regimen capable of stimulating insulin release (e.g., sulfonylurea). Combination therapy of a glitazone and sulfonylurea appears to be safe and well-tolerated and can result in significant and synergistic improvement in glycemic control. It should be noted that patients on maximum doses of a sulfonylurea should not be switched to glitazone monotherapy. Monotherapy should only be achieved if indicated by downward titration of the sulfonylurea dose. Finally, application of the results of this study should not be limited to patients who fail on maximum doses of sulfonylurea therapy but also extended to patients on lower doses of a sulfonylurea.

CONCLUSIONS

Troglitazone/glyburide combination therapy is well-tolerated and significantly ($p < 0.0001$) improves glycemic control over a 52-week period at doses of 200 mg/12 mg to 600 mg/12 mg compared with glyburide monotherapy in patients with NIDDM who are not adequately controlled on sulfonylurea therapy.

Additional examples of combination therapy according to this invention will employ the glitazone BRL 49653 together with a sulfonylurea selected from glyburide, chlorpropamide, tolbutamide, and glipizide. Another combination will be the glitazone TA 174 in combination with a sulfonylurea selected from glisoxepid, acetohexamide, glibornuride, and tolazamide. Still another combination provided by this invention is englitazone together with glibornuride, glyburide, or glisoxepid. These combinations produce synergistic glycemic control and will be utilized at doses which are synergistic. The synergistic combinations of this invention can also be utilized to treat conditions such as impaired glucose tolerance (IGT), thereby preventing or delaying the onset of frank NIDDM.

I claim:

1. A composition comprising from about 3 mg to about 250 mg of a sulfonylurea antidiabetic agent and from about 100 mg to about 1000 mg of a glitazone antidiabetic agent, said amounts of sulfonylurea and glitazone being synergistic for the treatment of non-insulin dependent diabetes mellitus in humans.

2. A composition of claim 1 wherein the sulfonylurea is selected from glisoxepid, glyburide, acetohexamide, chlorpropamide, glibornuride, tolbutamide, tolazamide, glipizide, gliclazide, gliquidone, glyhexamide, phenbutamide, and tolcyclamide.

3. A composition of claim 2 wherein the glitazone is selected from troglitazone, ciglitazone, pioglitazone, englitazone, TA 174, and BRL 49653.

4. A composition of claim 3 comprising troglitazone and glyburide.

5. A method of treating non-insulin dependent diabetes mellitus in humans comprising administering to a patient in need of treatment from about 3 mg to about 250 mg of a sulfonylurea antidiabetic agent in combination with about 100 mg to about 1000 mg of a glitazone antidiabetic agent, wherein said amounts are synergistic in the treatment of non-insulin dependent diabetes mellitus.

6. A method according to claim 5 wherein the sulfonylurea antidiabetic agent is selected from glisoxepid, glyburide, acetohexamide, chlorpropamide, glibornuride, tolbutamide, tolazamide, glipizide, gliclozide, gliquidone, glyhexamide, phenbentamide, and tolcyclamide.

7. A method according to claim 6 wherein the glitazone antidiabetic agent is selected from troglitazone, ciglitazone, pioglitazone, englitazone, TA 174, and BRL 49653.

8. A method according to claim 7 comprising a combination of glyburide and troglitazone.

* * * * *